(12) United States Patent (10) Patent No.: US 8,852,869 B2
Palarasah et al. (45) Date of Patent: Oct. 7, 2014

(54) METHOD OF DETERMINING FUNCTIONAL DEFICIENCIES IN THE COMPLEMENT SYSTEM

(75) Inventors: Yaseelan Palarasah, Odense C (DK); Mikkel Ole Skjødt, Frederiksberg C (DK); Lars Vitved, Odense C (DK); Claus Koch, Kobenhavn K (DK)

(73) Assignee: Immunobond ApS, Frederiksberg C (DK)

( * ) Notice: Subject to any disclaimer, the term of this patent is extended or adjusted under 35 U.S.C. 154(b) by 632 days.

(21) Appl. No.: 12/676,283

(22) PCT Filed: Sep. 5, 2008

(86) PCT No.: PCT/DK2008/050221
§ 371 (c)(1),
(2), (4) Date: Apr. 7, 2010

(87) PCT Pub. No.: WO2009/030240
PCT Pub. Date: Mar. 12, 2009

(65) Prior Publication Data
US 2010/0196927 A1 Aug. 5, 2010

(30) Foreign Application Priority Data
Sep. 5, 2007 (DK) .................................. 2007 01270

(51) Int. Cl.
G01N 33/00 (2006.01)
G01N 33/573 (2006.01)
G01N 33/53 (2006.01)
G01N 33/542 (2006.01)
G01N 33/564 (2006.01)

(52) U.S. Cl.
CPC .................................... *G01N 33/564* (2013.01)
USPC .............. 435/7.1; 435/7.4; 435/7.9; 435/7.92

(58) Field of Classification Search
None
See application file for complete search history.

(56) References Cited

FOREIGN PATENT DOCUMENTS

WO WO 2004/011674 A1 2/2004

OTHER PUBLICATIONS

Gadjeva et al. "Mannan-binding lectin—a soluble pattern recognition molecule" Molecular Immunology 41 (2004) 113-121.*
Printout from Chemindustry website at http://www.chemindustry.com/chemicals/028783504.html.*
Palarasah et al., "Functional capacity of the lectin pathway of the complement system," *Molecular Immunology* (2007): 3909-3994.
Von Zabern, I., "Action of polyionic substances on the complement system," *Activators and Inhibitors of Complement* (1993): 149-165.
Reynard. A.M., "The regulation of complement activity," *Journal of Immunopharmacology* (1980) 2(1): 1-47.
Palarasah et al., "SPS inhibits complement function," *J. Clin. Microbiol.* (2009): 1-27.
Lowrance et al., "Inactivation of the bactericidal activity of human serum by liquoid (sodium polyanethosulfonate),"*Applied Microbiology* (1969) 17 (6): 839-842.
Lipar-Ostir et al., "Electric conductivity of aqueous solutions of poly(antholesulfonic acid) and its alkaline salts," *J. Phys. Chem. B* (2009) 113: 2705-2711.
Loos et al., "Mode of interaction of different polyanions Immunology with the first (C1, C1) the second (C2) and the fourth (C4) component of complement," *Immunology* (1976) 31: 931-934.
Hall et al., "Comparision of sodium amylosulfate and sodium polyanetholsulfonate in blood culture media," *Journal of Clinical Microbiology* (1976) 3 (2): 212-213.
Edberg et al., "Inactivation of polyanionic detergent sodium polyanetholsulfonate by hemoglobin," *Journal of Clinical Microbiology* (1983) 18 (5): 1047-1050.
Traub et al., "Inactivation of classical and alternative pathway-activated bactericidal activity of human serum by sodium polyanetholsulfonate," *Journal of Clinical Microbiology* (1977) 5 (3): 278-284.
Roos et al., "Functional characterization of the lectin pathway of complement in human serum," *Molecular Immunology* (2003) 39: 655-668.
Gupta-Bansal et al., "Inhibition of complement alternative pathway function with anti-properdin monoclonal antibodies," *Molecular Immunology* (2000) 37: 191-201.
Petersen et al., "An assay for the mannan-binding lectin pathway of complement activation," *Jounral of Immunological Methods* (2001) 257: 107-116.

* cited by examiner

*Primary Examiner* — Daniel E Kolker
*Assistant Examiner* — James Rogers
(74) *Attorney, Agent, or Firm* — Merchant & Gould P.C.

(57) ABSTRACT

The present invention relates to a method of in vitro determining functional deficiencies in the lectin pathway of the complement system, the method comprises the steps of (a) diluting a mammalian sample of body fluid with a diluent comprising one or more inhibitors of the activation of the classical and the alternative pathways of the complement system; (b) activating the lectin pathway of the complement system in the sample obtained from (a); and (c) determining in the sample obtained from (b) the activation of one or more of the complement factors C3, C4, or one or more of the components of the C5-C9 complex. The invention furthermore relates to kits for use in connection with the above-mentioned method, the first kit comprises i) a first component comprising a carrier, one or more inhibitors of the classical and the alternative complement pathways and a diluent; and ii) a second component comprising one or more substances for activation of the lectin complement pathway and optionally an inert carrier. The second kit comprises a container comprising a predetermined amount of one or more inhibitors of the classical and the alternative complement pathways and a diluent, wherein the container is adapted for receiving a predetermined amount of sample, so that when the predetermined amount of sample is added, the concentration of the one or more inhibitors is an inhibitory effective concentration of the classical and alternative pathways, but not the lectin pathway.

40 Claims, 20 Drawing Sheets

METHOD OF DETERMINING FUNCTIONAL DEFICIENCIES IN THE COMPLEMENT SYSTEM

This application is a National Stage Application of PCT/DK2008/050221, filed Sep. 5, 2008, which claims benefit of Serial No. PA 2007 01270, filed Sep. 5, 2007 in Denmark and which applications are incorporated herein by reference. To the extent appropriate, a claim of priority is made to each of the above disclosed applications.

FIELD OF INVENTION

The present invention relates to assaying a particular pathway of the complement system. In particular a method of determining functional deficiencies in the lectin pathway of the complement system, said method comprises the steps of (a) diluting a mammalian sample of body fluid with a diluent comprising one or more inhibitors of the activation of the classical and the alternative pathways of the complement system; (b) activating the lectin pathway of the complement system; and (c) determining the activation of one or more of the complement factors C3, C4, or one or more of the components of the C5-C9 complex. The invention furthermore relates to kits for use in connection with the above-mentioned method.

BACKGROUND OF INVENTION

The complement (C) system is an important element in the innate immune system and functions as an enzyme cascade system and involves a large number of distinct plasma proteins and membrane proteins that react with one another in sequence to opsonize invading micro-organisms, to directly kill micro-organisms, and to induce an immediate series of inflammatory responses that help fight infections. The innate immune system differs from the part of the immune system termed the adaptive immune system, in that it does not confer long-lasting or protective immunity to the host, it is however important to stress that there are important links between the two parts of the immune system. The adaptive immune system is further divided into humoral and cellular components.

Uncontrolled activation of the complement system would result in damage to host cells. To prevent that the complement system for example is activated on host cells the system is regulated by regulatory complement factors either soluble plasma proteins or membrane bound proteins.

There are three distinct pathways through which the complement system can be activated. These pathways are termed the classical complement pathway (CP), the alternative complement pathway (AP), and the lectin complement pathway (or the mannan-binding pathway) (LP), and depend on different molecules and mechanisms for their initiation, but they converge to activate the same central effector molecule, C3, leading to fragments C3b and C3a.

The AP is initiated when C3b binds to a non-self surface, whereby cleavage and inactivation by the regulatory complement factor I is avoided. The AP initiation involves the complement factors C3b, factor B, factor D and Properdin.

The CP is initiated when multivalent binding of C1q to antigen-antibody complexes (immunocomplexes) is achieved, and involves the factors C1r, C1s, C2 and C4.

The LP is an ancient constituent of the complement system, probably predating the CP, and shares C2 and C4, with CP. However, initiation of the lectin pathway is antibody-independent with the difference lying in the initiation complex. The lectin pathway is activated when a collectin (MBL or ficolin) recognizes conserved patterns of carbohydrate structures on the surface of various microorganisms and furthermore involves MBL-associated serine proteases (MASP's).

MBL is an acute-phase protein; a modest 1.5 to 3 fold increasing in serum MBL concentration is seen after malaria infection and trauma (e.g, surgery). MBL is an oligomeric protein with an overall bouquet-like structure, resembling in this aspect C1q, and it belongs to the collectin family of proteins that consist of a collagen-like domain, an alfa coiled coil helical neck region and a carbohydrate recognition domain (CRD). It is through the CRD domain MBL exerts its functions by binding to carbohydrate structures on bacterial or viral surfaces.

Binding of MBL to a surface may by itself result in e.g. a microorganism being opsonized (facilitate fagocytosis), however, the activation of the lectin complement pathway is through activation of serine proteases (MASP's) linked to MBL (or ficolin). Four such serine proteases have been described, MASP1, MASP2, MASP3, and sMAP (sMAP is lacking a protease domain). In a recent study it has been demonstrated that in serum, proenzyme MASP-2 is entirely associated with MBL, whereas MASP-1 circulates in both bound and in unbound forms. The overall structures of MASPs resemble C1r and C1s and mimic their activities. Upon binding of MBL to carbohydrate structures on the surface of microbes, the proenzymes of MASP's are cleaved resulting in the active form. The activated MASP's are then able to exert their proteolytic activities against complement components. MASP-2 activates C4 and C2, and form the C3 convertase (C4bC2a) an effect similar to the effect of the CP C1s. Although MASP-1 is a more efficient peptidase than MASP-2, it does not display any efficient complement activation cleavage. However, it has been suggested that MASP-1 is involved in the complement activation through the direct cleavage of C3, but independent in vitro experiments showed that this is very unlikely. To date the exact function of MASP-3 and sMAP are unknown. It has been proposed that they may function as regulators of the MBL pathway activation through competitive inhibition of MASP-2 binding to MBL.

Serum concentrations of MBL are extremely variable ranging from almost 0 to 5 µg/ml in healthy humans. The low MBL concentrations are a consequence of polymorphism in the promoter region and/or in the structural part of the MBL gene.

The complement system is a major part of the immune defense against invading microorganisms, in particular during the early phase after pathogen entry. The AP and the LP will immediately be activated when foreign surfaces are recognized within the host. Together with other elements of the innate immune system recognition of "foreign" is also an essential element in the subsequent transport of microbial antigens to secondary lymphoid organs where lymphocyte stimulation occurs, leading to activation of the adaptive immune response with production of antibodies and effector T-lymphocytes as effector systems. Taken together, the complement system is required for optimal function of the host immune system.

Defects in the complement system may for example be due to genetic defects arising from mutations in the genes coding for individual complement components, or may for example be acquired defects, e.g., caused by excessive consumption of complement due to the presence of immune complexes or activators of AP (e.g. endotoxin), or caused by the presence of autoantibodies to complement factors, e.g. nephritic factor. Such defects in the complement system may result either in complete blockade of the involved complement pathway or in partial blockade leading to impaired function. Defects in particular components may also in some cases lead to impaired effector function of two or all three pathways.

Most deficiencies in the complement system may lead to diseases ranging from increased susceptibility to infections, to severe autoimmune manifestations etc. It is therefore of considerable clinical importance to be able to monitor the functions of the complement system, both as a diagnostic tool, but also as a prognostic marker and as a marker of disease activity.

Undesired activation of the complement system may lead to inflammation and tissue damage and can for example be seen in conditions such as autoimmune diseases, immune complex diseases, conditions with ischemia and in the course of host versus graft or graft versus host reactions.

Functional deficiencies in the lectin pathway are usually due to genetic polymorphisms in the MBL gene, but recently, deficiencies in the MASP genes and polymorphisms of Ficolin genes have also been reported. In general, genetic deficiencies of the complement system components are rare; an exception to this is MBL deficiency, which in human populations may occur with frequencies of 5-7%.

MBL deficiency is the most common inherited immunodeficiency (MBL concentration <100 ng/ml) with a prevalence of 5-7% in the general population. MBL deficiency has been investigated in many different populations and is largely explained by three single point mutations in codons 52, 54 and 57 of exon 1 of the MBL gene. These mutations are also frequently referred to as variants D, B and C, respectively, with variant A representing wild type. These mutation-frequencies are different among populations. In Eurasian populations the B variant mutation make up 22-28%, whereas the C variant mutation is characteristic of sub-Saharan African populations making up 50-60%. Finally, the D mutation makes up 14% in European populations. A common result of the mutations in the exon 1 MBL gene is an impaired oligomerization, which leads to a functional deficiency of the MBL protein. Several studies show that MBL deficiency is associated with increased susceptibility to many infectious diseases, namely extracellular pathogens and particularly organism which cause acute respiratory tract infections during early childhood. However, studies also indicate that pathology arising from MBL deficiency may require one or more co-existing immune deficits. For example, recent studies on *Neisseria menigitidis* disease show an increased probability of the disease when MBL deficiency is associated with a properdin defect. In order to give the correct and most efficient treatment in relation to disorders, conditions, diseases and/or genetic deficiencies in the immune system, it is of paramount importance to identify where the e.g. disorder is located.

In the past, complement function has been measured through haemolytic assays which enable functional assessment of the classical (CP) and the alternative (AP) complement pathways through their ability to generate the membrane attack complex (C5b-9) upon activation. Similar assays for the lectin pathway, are currently not available. In general, the available assays are cumbersome and tedious, and more easy-to-perform assays are required.

A similar assessment of the lectin complement pathway function is hampered by interference from activation of the classical and the alternative complement pathway. Activation of the lectin complement pathway requires an activating surface with carbohydrate structures, and most often there will in the activation phase be interference from anti-carbohydrate antibodies from the test sample giving rise to activation of the classical complement pathway, and from a direct activation of the alternative complement pathway due to the presence of a non-self surface. Therefore, a reliable assay must prevent the concomitant activation of these two pathways.

Until now, at least three assays have been described for determining functional deficiencies in the lectin complement pathway. One assay measures the functional activity of lectin-MASP complex through activation of added exogenous C4. Another assay measures endogenous activation of C4 after blocking of classical and alternative complement activation by using a high ionic strength dilution buffer (1M NaCl) (Petersen S V, Thiel S, Jensen L, Steffensen R, Jensenius J C.: An assay for the mannan-binding lectin pathway of complement activation. J Immunol Methods. 2001; 257:107-16). Finally, a lectin pathway assay uses a monoclonal antibody to C1q to inhibit classical complement activation, and activation of the alternative complement pathway is inhibited either through dilution or by an antibody to complement factor D (Roos A, Bouwman L H, Munoz J, Zuiverloon T, Faber-Krol M C, Fallaux-van den Houten F C, Klar-Mohamad N, Hack C E, Tilanus M G, Daha M R.: Functional characterization of the lectin pathway of complement in human serum. Mol Immunol. 2003; 39:655-68).

In the previously known methods the complement pathways are for example severely influenced by the use of 1M NaCl buffers, and the use of a monoclonal antibody to C1q does not exclude interactions via the AP. Furthermore, the previously known methods are in general cumbersome, expensive and influenced by the AP and the CP. Accordingly, an easy-to-perform and reliable method for determining potential functional deficiencies in the lectin pathway of the complement system is needed.

SUMMARY OF INVENTION

The present invention relates to a method of in vitro determining functional deficiencies in the lectin pathway of the complement system. The present inventors have surprisingly found a method to inhibit the classical and the alternative pathway so that it is possible to measure the activity of the lectin pathway. The method is an in vitro method of determining the functional deficiencies in the lectin pathway of the complement system, the method comprises the steps of (a) diluting a mammalian sample of body fluid with a diluent comprising one or more inhibitors of the activation of the classical and the alternative pathways of the complement system; (b) activating the lectin pathway of the complement system in the sample obtained from (a); and (c) determining in the sample obtained from (b) the activation of one or more of the complement factors C3, C4, or one or more of the components of the C5-C9 complex.

The invention furthermore relates to kits for use in connection with the above-mentioned method, the first kit comprises i) a first component comprising a carrier, one or more inhibitors of the classical and the alternative complement pathways and a diluent; and ii) a second component comprising one or more substances for activation of the lectin complement pathway and optionally an inert carrier. The second kit comprises a container comprising a predetermined amount of one or more inhibitors of the classical and the alternative complement pathways and a diluent, wherein the container is adapted for receiving a predetermined amount of sample, so that when the predetermined amount of sample is added, the concentration of the one or more inhibitors is an inhibitory effective concentration of the classical and alternative pathways, but not the lectin pathway.

DETAILED DESCRIPTION OF THE INVENTION

Figure 1:
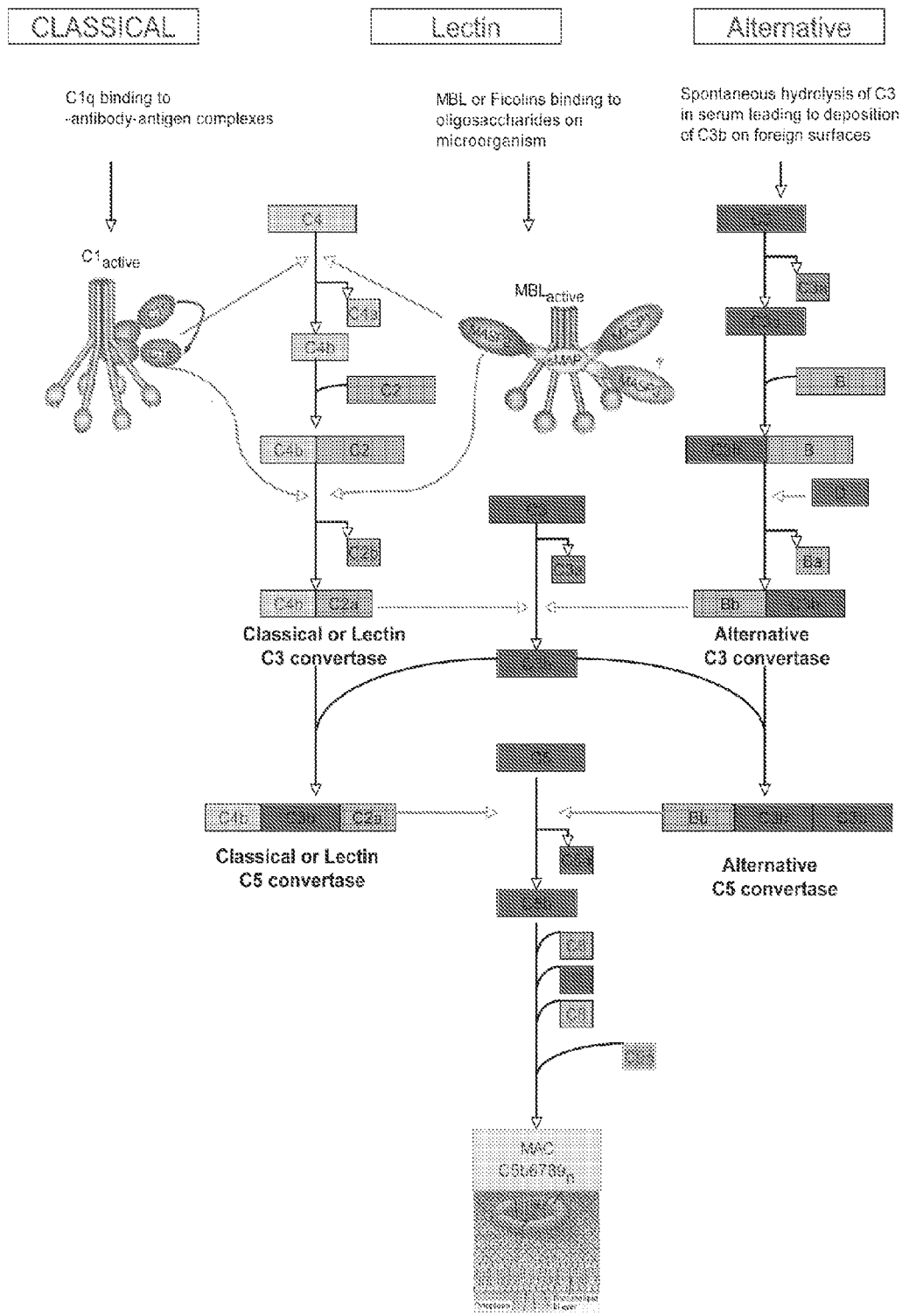
FIG. 1 shows a schematic overview over the three pathways of the complement system, with their activation and effect on the various cascade reactions: the classical, the lectin, and the alternative pathways, respectively, together with their common terminal complex.
Figure 2:
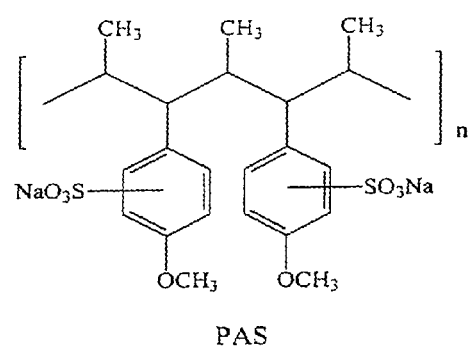
FIG. 2 shows the structural formula of the sulfonic acid polymer, polyanetholesulfonic acid sodium salt (PAS).
Figure 3A:
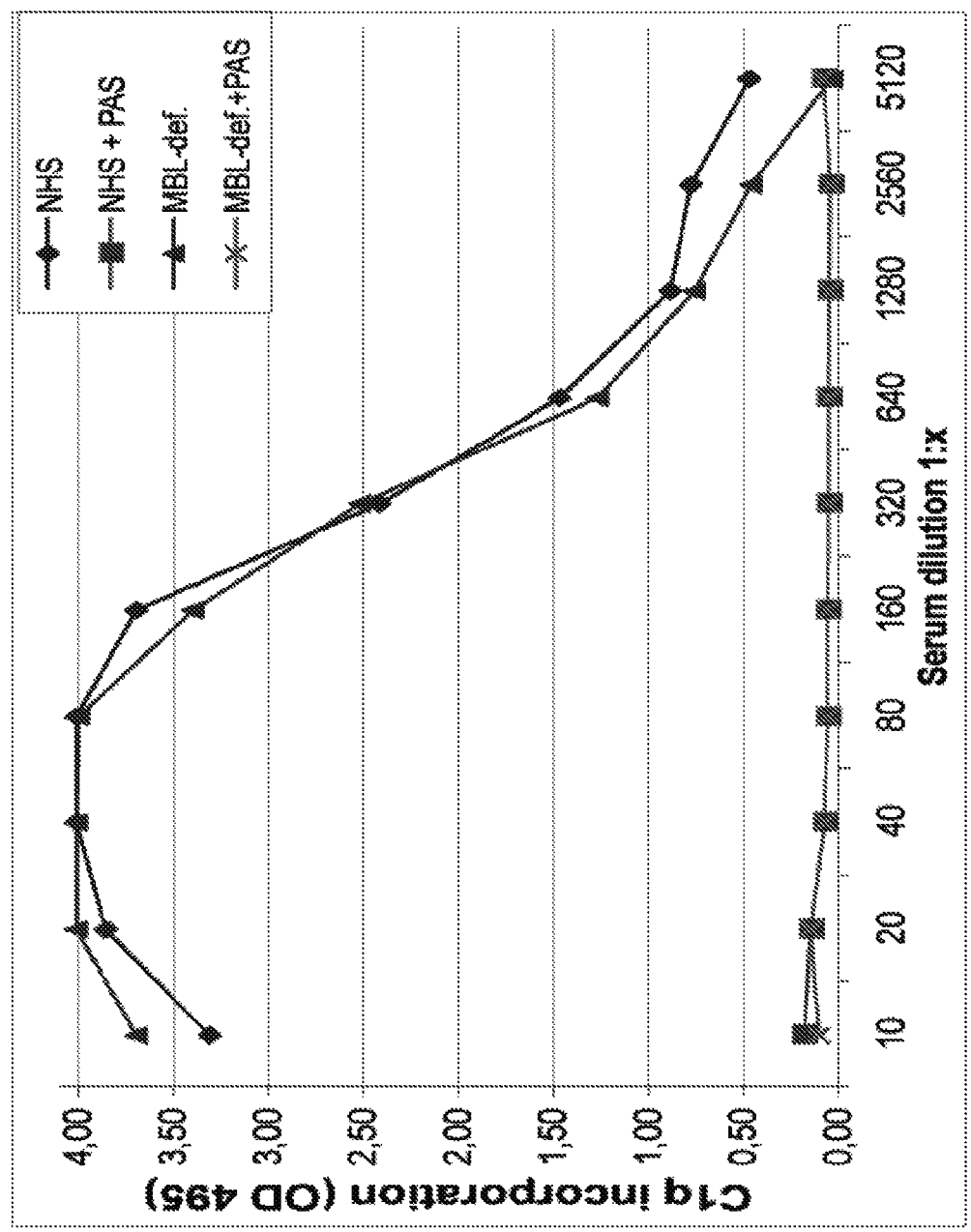
FIG. 3 shows classical complement activation induced by immune-complexes. Different concentrations of NHS or MBL-deficient serum in the presence or absence of PAS (500 μg/ml) were incubated on microtiter plates coated with IC (a-d). Activation and deposition of complement factors C1q, C4, C3 and C9 were assessed using specific monoclonal antibodies with specificity for the individual factors.
Figure 3B:
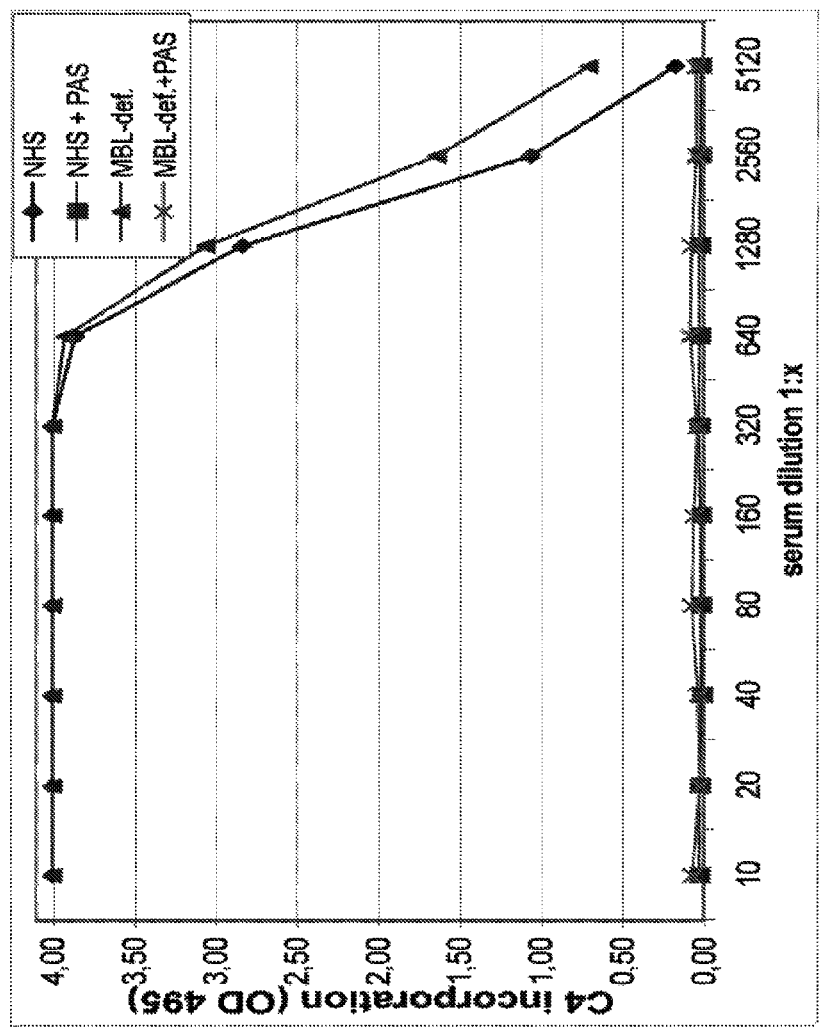
Figure 3C:
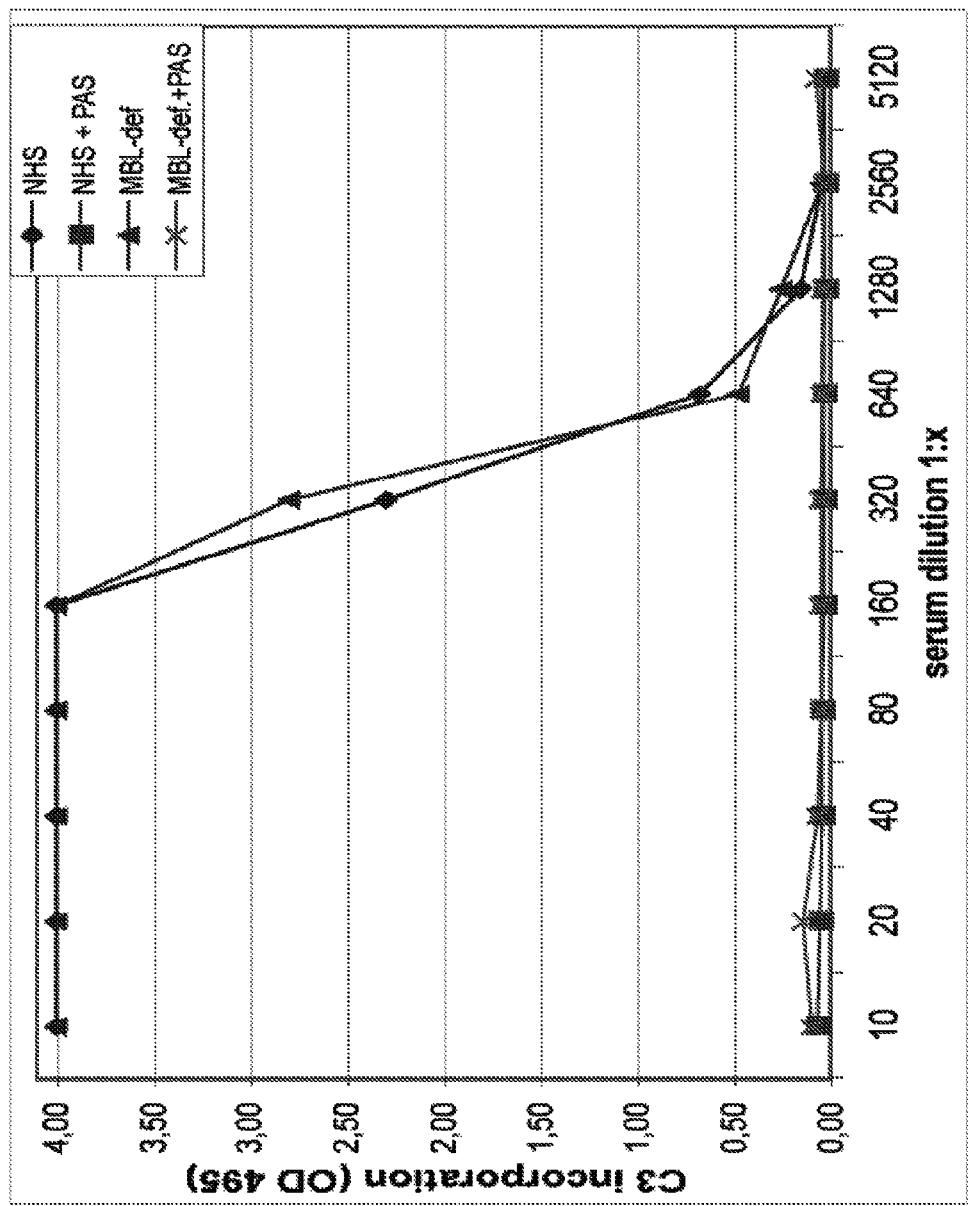
Figure 3D:
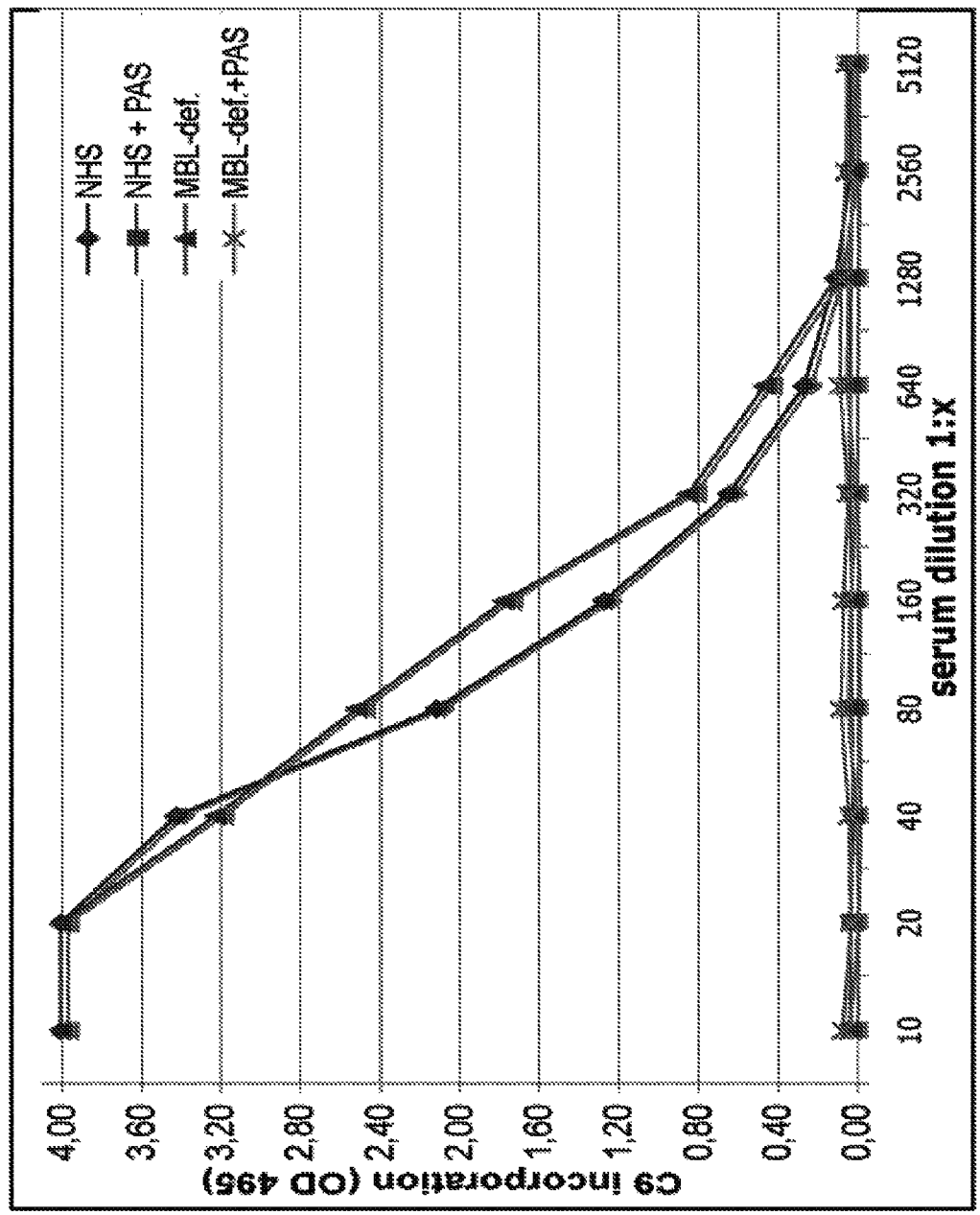

The present inventors have surprisingly found that they can avoid the interactions from the classical and the alternative complement pathways during a functional analysis of the lectin complement pathway. Accordingly, the present invention relates to a method and a kit for determining functional deficiencies in the lectin pathway of the complement system, wherein the activation of the classical and the alternative complement pathways are inhibited by the addition of an inhibitor affecting only the classical and alternative pathways and not the lectin pathways. The method and the kit are for in vitro analysis.

In one aspect of the present invention the method for in vitro determining functional deficiencies in the lectin pathway of the complement system, the method comprises the steps of:
(a) diluting a mammalian sample of body fluid with a diluent comprising one or more inhibitors of the activation of the classical and the alternative pathways of the complement system;
(b) activating the lectin pathway of the complement system in the sample obtained from (a); and
(c) determining in the sample obtained from (b) the activation of one or more of the complement factors C3, C4, or one or more of the components of the C5-C9 complex.

In a method according to the invention the mammalian sample may for example be a human sample of body fluid, such as e.g., a sample of blood, serum or plasma, or any other available biological fluid. A blood or serum sample may be used directly in step (a). Samples of e.g. plasma heparin may also be used directly, whereas samples of e.g. plasma citrate or plasma EDTA may be added calcium prior to dilution. In some embodiments of the present invention the preferred body fluid is blood, whereas in other embodiments the preferred body fluid is serum. These mammalian samples can be obtained by any well-know methods that will be apparent to a skilled person.

The present inventors have surprisingly found that one or more polyanions can be applied to inhibit the activation of the classical (CP) and the alternative (AP) complement pathways. The activation of the classical and the alternative complement pathways is inhibited by interference with at least one component/molecule essential to the CP and AP activities. A hypothesis for the observed inhibitory effect evolves around an inhibition of proteases essential for activation of the CP and AP, this could for instance be serine proteases. Especially, polyanions such as sulphated polyanions can be used in accordance with the present invention to selectively inhibit the classical and the alternative component pathways. Non limiting examples of the one or more sulphated polyanions are polyanethol sulphonate (PAS), a lower weight heparin, a dextransulphate, a sulphated carragenan, chondroitin sulphate or mixtures thereof. In a preferred embodiment of the present invention the one or more inhibitors is a sulphated polyanion, and in a more preferred embodiment of the invention at least one of the one or more inhibitors is the sulphated polyanion polyanethole sulphonate (PAS). In other embodiments of the present invention mixtures of the polyanions is applied to achieve a synergistical effect. Said mixture could for instance be a mixture of PAS and a lower weight heparin.

In the method according to the invention, the mammalian sample to be analyzed is diluted with an appropriate diluent comprising the one or more inhibitors. In one embodiment of the method according to the invention, the concentration of the one or more inhibitors is an inhibitory effective concentration. The one or more inhibitor may e.g. be present in a concentration range of from about 50 to about 1000 μg/ml, such as e.g., from about 100 to about 900 μg/ml, from about 200 to about 800 μg/ml, or preferably from about 300 to about 700 μg/ml. The concentration range is a so-called concentration window. However, the applicable concentration range will be dependent on the specific inhibitor applied.

Polyanethol sulfonic acid (PAS) may be used as an inhibitor of the classical and the alternative complement pathways, without significantly affecting the lectin complement pathway. PAS has for decades been used as an additive to blood samples intended for analysis of bacteriaemia in patients suspected of developing sepsis, or in blood samples from patients with symptoms of sepsis. Blood from such patients has been drawn under sterile conditions into bottles containing growth medium for culture of bacteria, and containing PAS as an anticoagulant. Later on it was realised that PAS also functions as an inhibitor of cellular and humoral elements in the blood that might interfere with bacterial growth.

PAS (under the trade-name Liquoid) is usually used in a concentration of 125 or 250 µg/ml in growth medium, and has been shown to interfere with both complement-dependent killing of bacteria and with cell-dependent killing. Some studies have previously demonstrated that PAS functions through an activation of the complement system, while other studies have indicated an inhibition of complement activation.

The present inventors have analyzed the effect of PAS on the individual complement system pathways. The assays for the three individual complement pathways (CP assayed on immunocomplex-coated ELISA-plates, AP assayed on LPS-coated surfaces, and LP assayed on mannan-coated surfaces) showed that—within a certain concentration range—PAS would totally inhibit the CP and the AP but not affect the LP. Experimental data are shown in the Examples. The inhibition by PAS is dose dependent, thus PAS is preferably used in a concentration above a low non-inhibitory concentration and below a high concentration, wherein said high concentration inhibits all components. Said concentration range is a so-called concentration window. In a preferred embodiment of the present invention PAS is applied in a diluent in a concentration range of from about 300 to about 700 µg/ml. In a more preferred embodiment of the invention the concentration is in a range of from about 400 to about 600 µg/ml, and in an even more preferred embodiment, the concentration of PAS in the diluent is about 500 µg/ml. In another embodiment of the invention, mixtures of one or more inhibitor are applied to broaden the concentration range wherein the activation of the classical and the alternative complement pathways are inhibited but the lectin complement pathway is not. This could for instance be a mixture of PAS and a heparin, such as a low molecular weight heparin.

In one embodiment of the method according to the present invention, the diluent for diluting the mammalian sample is an aqueous media, such as e.g. a buffered aqueous media, a buffered isotonic aqueous media. Non-limiting examples of buffers that may be used in a diluent in accordance with the present invention may be selected from the group consisting tris-buffer, hepes buffer and mixtures thereof. However the person skilled in the art will be able to identify other suitable buffers. In one embodiment of the invention, the diluent is buffered to a pH-value of about physiological pH with a buffer. The diluent may furthermore contain $Ca^{2+}$ and $Mg^{2+}$. Preferably, the concentrations of $Ca^{2+}$ and $Mg^{2+}$ are in ranges of from about 2 to about 6 mM, and from about 0.5 to about 4 mM, respectively. The concentrations of $Ca^{2+}$ and $Mg^{2+}$ are more preferably in ranges of from about 3 to about 5 mM, and from about 1 to about 3 mM, respectively; and the concentrations of $Ca^{2+}$ and $Mg^{2+}$ are even more preferably about 4 mM, and about 2 mM, respectively. As a skilled person will recognize, to maintain the optimal assay conditions the diluent may furthermore be an isotonic diluent with at pH-value about the physiological pH range.

In accordance with a method of the present invention, the diluent may furthermore comprise Tween, such as e.g., Tween 20, in a concentration range of from about 0.01% to about 0.50%, such as e.g., about 0.02% to about 0.40%, about 0.02% to about 0.30%, about 0.02% to about 0.20%, about 0.03% to about 0.10%, and preferably at a concentration of about 0.05%. In a preferred embodiment the diluent comprises Tween 20 in a concentration of about 0.05%.

In a preferred embodiment of the invention, the diluent is a buffered aqueous media comprising $Ca^{2+}$ and $Mg^{2+}$ in concentrations of about 4 mM, and about 2 mM, respectively, and comprising Tween 20 in a concentration of about 0.05%.

In the method according to the invention, the dilution in step (a) may be performed with or without an incubation time, i.e., the dilution and hereby the inhibition occurs substantially instantaneous. However, in some instances an incubation at e.g. room temperature may be used, the incubation time may then be e.g. less than 30 min, such as e.g., less than 20 min or less than 10 min. After dilution, the activation of the classical and the alternative complement pathways are inhibited by the inhibitor, hereby allowing the subsequent activation step to be unaffected by activation of the classical and the alternative complement pathways.

In the method according to the invention the activation in step (b) may be performed by contacting the sample obtained from (a) with various components that lead to activation of the lectin complement pathway. The activation is antibody-independent and is initiated when a collectin (MBL or ficolin) recognizes conserved patterns of carbohydrate structures on the surface of various microorganisms and furthermore involves MBL-associated serine proteases (MASP's). In one embodiment of the invention the activation in step (b) is performed by contacting the sample obtained from (a) with a lectin binding surface comprising carbohydrate structures. In another embodiment of the invention step (b) is performed by contacting the sample obtained from (a) with a MBL binding surface, preferably a mannan. In another embodiment step (b) is performed by contacting the sample obtained from (a) with a ficolin binding carbohydrate.

The activation in step (b) may for example be performed with an incubation time of from about 10 minutes to about 3 hours, and preferably with an incubation time of from about 30 minutes to about 2.5 hours, more preferably with an incubation time of from about 45 minutes to about 2 hours, and even more preferably with an incubation time of about 90 minutes. To give the optimal conditions for the activation, the activation may be performed at an incubation temperature of about 37° C.

In the method according to the invention step (c) relating to determining the activation of the complement factors C3, C4, or one or more of the components of the C5-C9 complex, may be performed by contacting the sample obtained from (b) with an antibody to one or more of the activated complement factors C3 or C4, or one or more of the components of the C5-C9 complex. In one embodiment of the invention the antibody is directly labelled with a signal molecule, i.e. the antibody is a labelled antibody. Non-limiting examples of labels that may be used to label the antibody is a fluorescent label, such as e.g., a lanthanide like europium or Horse radish peroxydase, an enzyme label, such as e.g., a peroxidase or alkaline phosphatase or a radioactive isotope, such as e.g., $I^{125}$. In a preferred embodiment of the invention step (c) relates to determining the activation of one or more of the complement factors C3 and C4; and in a more preferred embodiment of the invention, step (c) relates to determining the activation of the complement factor C3. As described above, this may be performed by contacting the sample obtained from (b) with an antibody to one or more of the activated complement factors C3 or C4, or an antibody to C3, respectively.

A method according to the invention may further comprise a step (d) wherein the anti-C3, -C4, or -C5-C9 complexes obtained in step (c) may be detected by the use of labelled anti-antibodies against one or more of the anti-C3, or -C4, or against antibodies against one or more of the components of the C5-C9 complex. Accordingly, an anti-antibody labelled with e.g. a fluorescent label or an enzyme label, may be used for all the anti-C3, -C4, or -C5-C9 complexes instead of using several specific fluorescent or enzyme labelled anti-antibodies, one for each anti-Cx complex. A skilled person will recognize that if step (c) is followed by a step (d), then there may be an intermediary washing, wherein a washing solution is used. Said washing solution may e.g. be the diluent without inhibitor, or a buffer-part of the diluent, if any. In one embodiment, the washing solution is an isotonic aqueous media buffered to physiological pH and further comprising 0.05% Tween 20. In a preferred embodiment of this further optional step (d) the one or more anti-C3 or anti-C4 complexes obtained in step (c) is detected by the use of labelled anti-antibodies against one or more of the anti-C3 or anti-C4. In a more preferred embodiment of step (d) anti-C3 complexes obtained in step (c) is detected by the use of labelled anti-antibodies against anti-C3.

In a method according to the invention step (c) may further comprise comparing the determined activation level of one or more of the complement factors C3, C4, or one or more of the components of the C5-C9 complex with a reference level. Preferably the reference level is an average value obtained from healthy individuals.

As used herein the term "healthy individuals" is intended to mean individuals with no apparent disease. Among the general population are approximately 20-25% who have deficiencies in the lectin pathway arising from mutations, this may for example be individuals heterozygous for MBL structural mutations, i.e. wild-type gene (A) on one chromosome, and a structural mutation (B, C, or D) on the other chromosome; or for example individuals homozygous for mutations for one single or combinations of the structural mutations B, C, and D. Another kind of mutations is promoter region mutations. Preferably an average value is obtained from a group of healthy individuals where individuals heterozygous or homozygous for MBL structural mutations have been identified and excluded, this group of individuals is denoted "healthy individuals". More preferably an average value is obtained from a group of healthy individuals where individuals with deficiencies arising from mutations, i.e. for example both promoter region mutations and MBL structural mutations, have been identified and excluded, this group of individuals is denoted "healthy individuals".

Alternatively, a reference level may be an average value obtained from the general healthy population. As used herein the term "the general healthy population" is intended to mean individuals with no apparent disease but possibly with mutations in the lectin pathway as described immediately above here.

In one embodiment of the invention, the determined activation level of one or more of the complement factors C3, C4, or one or more of the components of the C5-C9 complex is compared with a reference level obtained as an average value from healthy individuals, wherein an activation level at least 50% lower than the reference level is indicative of a functional deficiency in the lectin pathway. In preferred version of this embodiment an activation level at least 55% lower than the reference level is indicative of a functional deficiency in the lectin pathway, such as e.g. at least 60% lower, at least 65% lower, at least 70% lower, or at least 75% lower. Most preferably an activation level at least 65% lower than the reference level, obtained as an average value from healthy individuals is indicative of a functional deficiency in the lectin pathway. See for instance FIG. 11.

In one embodiment of the invention, the determined activation level of one or more of the complement factors C3, C4, or one or more of the components of the C5-C9 complex is compared with a reference level obtained as an average value from the general healthy population, wherein an activation level at least 20% lower than the reference level is indicative of a functional deficiency in the lectin pathway. In preferred version of this embodiment an activation level at least 30% lower than the reference level is indicative of a functional deficiency in the lectin pathway, such as e.g. at least 35% lower or at least 40% lower, even more preferred an activation level at least 45% lower than the reference level, such as e.g. at least 50% lower. Most preferably an activation level at least 55% lower than the reference level, such as e.g. at least 60% lower, obtained as an average value from the general healthy population is indicative of a functional deficiency in the lectin pathway. See for instance FIG. 10.

In another aspect, the present invention relates to a kit that may be used in connection with the method for in vitro determining functional deficiencies in the lectin pathway of the complement system, said kit comprises
  i) a first component comprising a carrier, one or more inhibitors of the classical and the alternative complement pathways and a diluent; and
  ii) a second component comprising one or more substances for activation of the lectin complement pathway and optionally an inert carrier.

In one embodiment of a kit according to the present invention, the one or more inhibitors of the first component are contained inside the carrier. Said carrier may for example be a container, such as e.g., a vial, a sample vial, an evacuated vial or a blood sample vial.

In another embodiment of a kit according to the presents invention the one or more substances of the second component is coated onto at least part of an inert carrier. This inert carrier to be used in the second component may for instance comprise an inert rod, stick, plate, or sphere adapted to fit inside the container.

As described above in connection with the method according to the present invention, at least one of the one or more inhibitors of the classical and the alternative complement pathways may be a polyanion, preferably a sulphated polyanion, and even more preferably polyanethol sulphonate. Non-limiting examples of the one or more inhibitors, concentration ranges of the inhibitor, together with non-limiting examples of the diluent are described above in connection with the method according to the invention.

The activation of the lectin complement pathway is performed by the one or more substances in the second component; in one embodiment of the kit according to the invention at least one of the one or more substances of the second component is a lectin binding surface comprising carbohydrate structures. In another embodiment, at least one of the one or more substances of the second component is a MBL-binding carbohydrate, preferably a mannan. In another embodiment at least one of the one or more substances of the second component is a ficolin-binding carbohydrate.

A kit according to the presents invention may further comprise iii) a third component comprising an antibody to one or more of the complement factors C3 or C4, or one or more of the components of the C5-C9 complex and optionally a carrier. This antibody of the third component may for some methods of detection be a labelled antibody, wherein the label e.g. is an enzyme label, such as e.g., a peroxidase or alkaline phosphatase, or a fluorescent label, such as e.g., a lanthanide like europium or horse radish peroxydase.

A kit according to the present invention may further comprise iv) a fourth component comprising a labelled anti-antibody against the anti-C3, and -C4, or against antibodies against one or more of the components of the C5-C9 complex. An anti-antibody labelled with e.g. a fluorescent label, may be used for all the anti-C3, -C4, or -C5-C9 complexes instead of using several specific fluorescent labelled anti-antibodies one for each anti-Cx complex.

Furthermore, a kit according to the present invention may further, for some methods of detection, comprise v) a fifth component comprising an enzyme substrate and optionally a carrier. Non-limiting examples of enzyme substrates are peroxidase substrates, hydrogenperoxide ($H_2O_2$), OPD (o-Phenylenediamine dihydrochloride) and TMB (3,3',5,5'-Tetramethylbenzidine). In an embodiment of the invention applying enzyme labelled antibodies, the enzyme substrate for the enzyme is incubated with the sample and allowed to react for e.g. 30 min, after which colour development is measured e.g. using an ELISA-reader.

In another embodiment of a kit according to the invention, the kit further comprises vi) a sixth component comprising a washing solution. A non-limiting example of a washing solution is an aqueous media buffered to physiological pH with tris or hepes buffer and further comprising 0.05% Tween 20.

A method and a kit according to the present invention may be carried out in an ELISA-format, but other assay types, including the use of other signal molecules or e.g. homogenous assay formats may be used. In relation to a method and a kit according to the present invention, normal standards, and positive and negative controls may be used. For instance, as a calibrator/normal standard a normal body liquid may be used, such as e.g., a pool of serum, preferably adjusted with an international standard for LP activity. As a negative control may for instance be used a sample treated in order to destroy all complement activity, e.g. by heat treatment, or preferably a sample from donors with undetectable LP activity, such as from an individual with complete deficiency of the lectin complement pathway. When such standards and controls are used, the sample and the standards, negative and positive controls are diluted in the same way in the diluent, preferably by mixing equal volumes of sample and diluent containing the one or more inhibitors of the classical and the alternative pathways.

Depending on the detection method applied, e.g. fluorescent label, enzyme label or other suitable labels, a low read-out will indicate a deficiency in the lectin complement pathway. When fluorescent labels are applied this is e.g. low absorbance intensity. A low read-out may for instance be a value corresponding to the negative control.

A further aspect of the present invention relates to a kit comprising a container comprising a predetermined amount of one or more inhibitors of the classical and the alternative complement pathways and a diluent, wherein the container is adapted for receiving a predetermined amount of sample, so that when the predetermined amount of sample is added, the concentration of the one or more inhibitors is an inhibitory effective concentration of the classical and alternative pathways, but not the lectin pathway.

In one embodiment of the above-mentioned kit, the container is a vial, such as preferably an evacuated vial adapted for receiving the predetermined amount of sample.

As described above in connection with the method according to the present invention, at least one of the one or more inhibitors of the classical and the alternative complement pathways may be a polyanion, preferably a sulphated polyanion, and even more preferably polyanethol sulphonate. Non-limiting examples of the one or more inhibitors, concentration ranges of the inhibitor, together with non-limiting examples of the diluent are described above in connection with the method according to the invention.

In one embodiment of the above-mentioned kit, the container is adapted for receiving an inert carrier coated with one or more substances for activation of the lectin complement pathway. Said inert carrier may comprise an inert rod, stick, plate, sphere adapted to fit inside the container. Non-limiting examples of the one or more substances for activation of the lectin complement pathway is as described above in connection with the method according to the invention.

The features mentioned above for a method of in vitro determining functional deficiencies in the lectin pathway of the complement system apply mutatis mutandis for the kits according to the present invention, and vice versa.

The method of the present invention will now be further illustrated in the below examples showing the inhibition of CP activation by incubating the sample with PAS (Example 1), the inhibition of AP activation by incubating the sample with PAS (Example 2), and finally an example (Example 3) showing the undisturbed activation of LP in the presence of the preferred concentration of PAS. However, the invention is by no means intended to be limited by the following examples.

EXAMPLES

Example 1

Assessment of Functional Capacity of the Classical Pathway

The following setup in order to measure the functional capacity of the CP was used: Human serum albumin (HSA) was dissolved in PBS (10 mg/ml) and stored at 4° C. Maxisorp microtiter plates (Nunc, Roskilde, Denmark) were coated with 100 µl HSA (10 µg/ml) in coating buffer (o/n at 4° C. The plates were emptied, 3× washed and the residual binding sites were blocked by incubation with 0.05% Tween-TBS for 1 hour at RT. After blocking the plates were incubated o/n at RT with 100 µl rabbit anti-human serum albumin, diluted 1:1000 in dilution buffer. The plates were emptied, 3× washed and test-serum diluted in dilution buffer containing 4 mM $Ca^{2+}$, 2 mM $Mg^{2+}$, and 0.05%-Tween-20 was incubated for 90 min at 37° C. After 3× wash, the plates were incubated with 100 µl of the appropriate MAb against human complement component and incubated for 60 min at 37° C. After 3× wash, the plates were incubated at RT for 60 min with 100 µl HRP-conjugated rabbit anti-mouse immunoglobulin (P260, DAKO, Glostrup) diluted 1:1000 in dilution buffer (with shaking).

PAS and the Activity of Classical Complement

The functional capacity of CP was analyzed on IC-coated surfaces. ELISA-plates were coated with human albumin and subsequently incubated with a rabbit anti human albumin, followed by incubation with dilutions of human sera.

NHS or MBL-deficient serum was incubated in the presence or absence of PAS and the incorporation of the C components C1q, C4, C3 and C9 was measured using specific mAbs to the individual complement components. The results from these experiments are shown in FIG. 3.

Incubation of dilutions of NHS or MBL-deficient serum on solid phase IC resulted in a dilution-dependent deposition of C1q, C4, and C3 to the IC. Binding of these C components was completely absent in the presence of PAS in a final concentration of 500 µg/ml. The inhibition of C1q-binding to IC could well explain the overall effect on the CP. Thus, PAS inhibit CP dependent complement activation.

Figure 4:
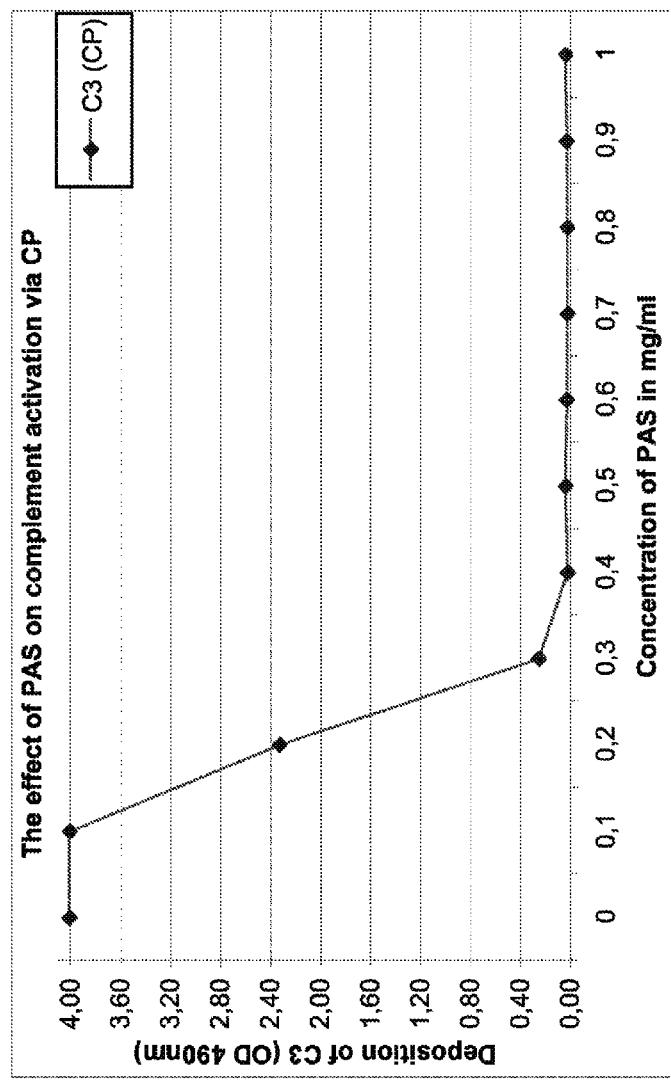
FIG. 4 shows a dose-response curve for the effect of PAS on activation of classical complement functional activity.

Dose-Response Curve for the Inhibition of Classical Complement Functional Activity by PAS Various concentrations of PAS were used in order to determine a dose-response curve for PAS. Experiments were performed as described above only with varying the amount of PAS added to the sample. PAS-concentrations >300 µg/ml completely inhibited C3 deposition. Only an example where deposition of C3 is measured is shown, but identical results were obtained when C4 or C9 deposition were analysed. FIG. 4 shows the dose-response curve.

Example 2

Assessment of Functional Capacity of the Alternative Pathway

The protocol for the functional capacity of the AP was similar to the method for the CP assay, with the following modification: Lipopolysaccharide W *S. typhimurium* (10 ug/ml) (lot. 51974, DICO LABORAORIES, US) was coated in 1M NaCl and used as activating surface for AP activation. The serum samples were diluted in dilution buffer with 4 mM $Mg^{2+}$, 10 mM EGTA, and 0.05% Tween-20 and were incubated for 60 min at 37° C. The C3, properdin and C9 deposition was measured by adding 100 µl of mAbs.

PAS and the Activity of Alternative Complement

Figure 5A:
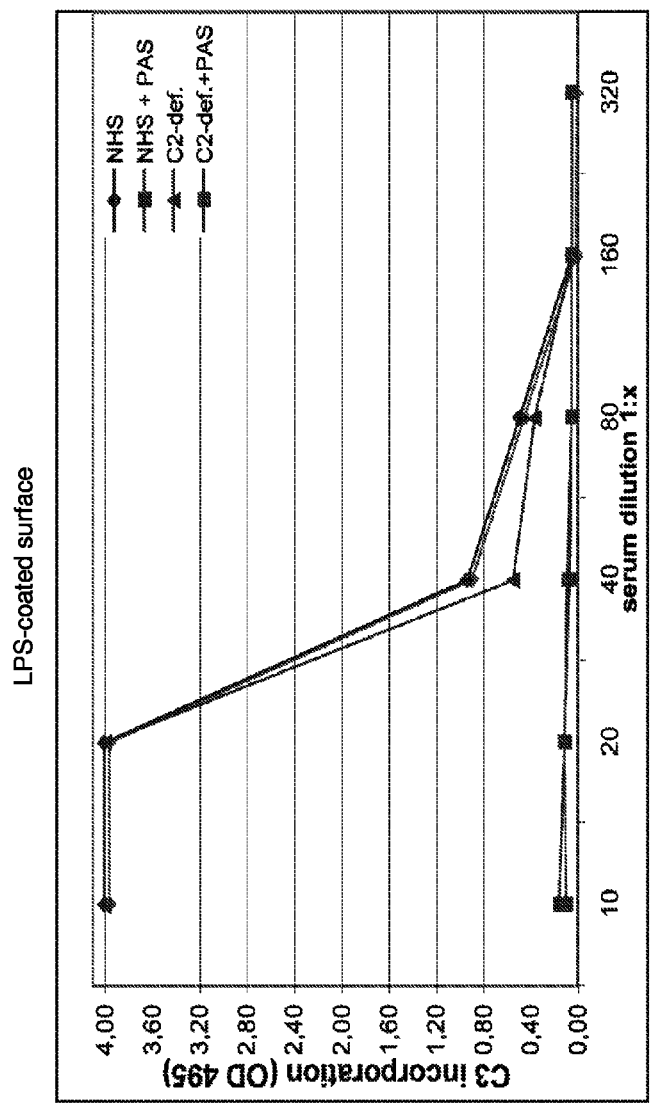
FIG. 5 shows the activation of the alternative pathway on an LPS-coated surface. Dilutions of NHS and C2-deficient serum in $Mg^{++}$-EGTA-buffer were incubated on plates coated with LPS in the presence or absence of PAS. Deposition of C3 (A), Properdin (B) and C9 (C) was subsequently assessed. Deposition of all three complement components was reduced to background levels when 10 mM EDTA was present in the dilution buffer (not shown).
Figure 5B:
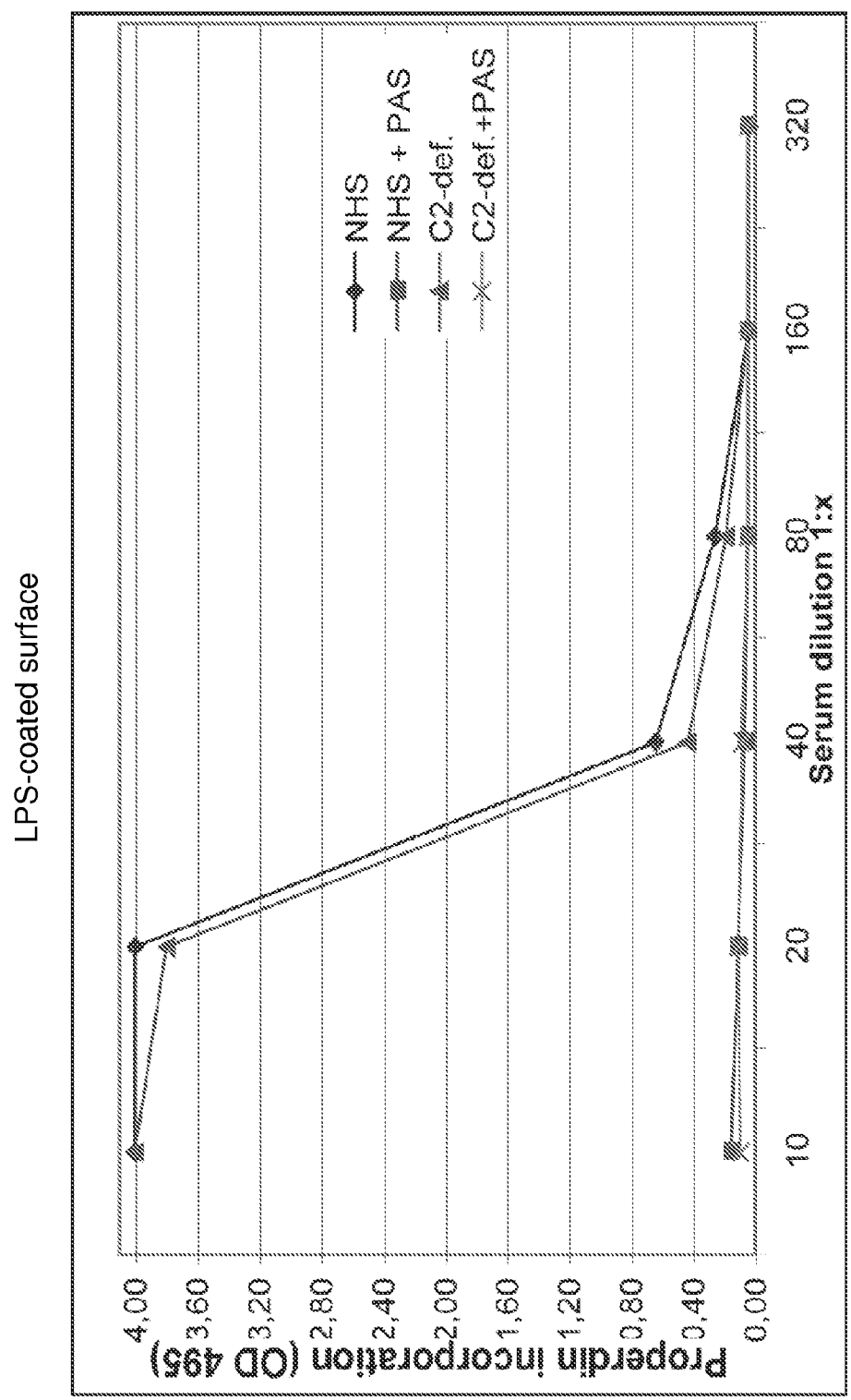
Figure 5C:
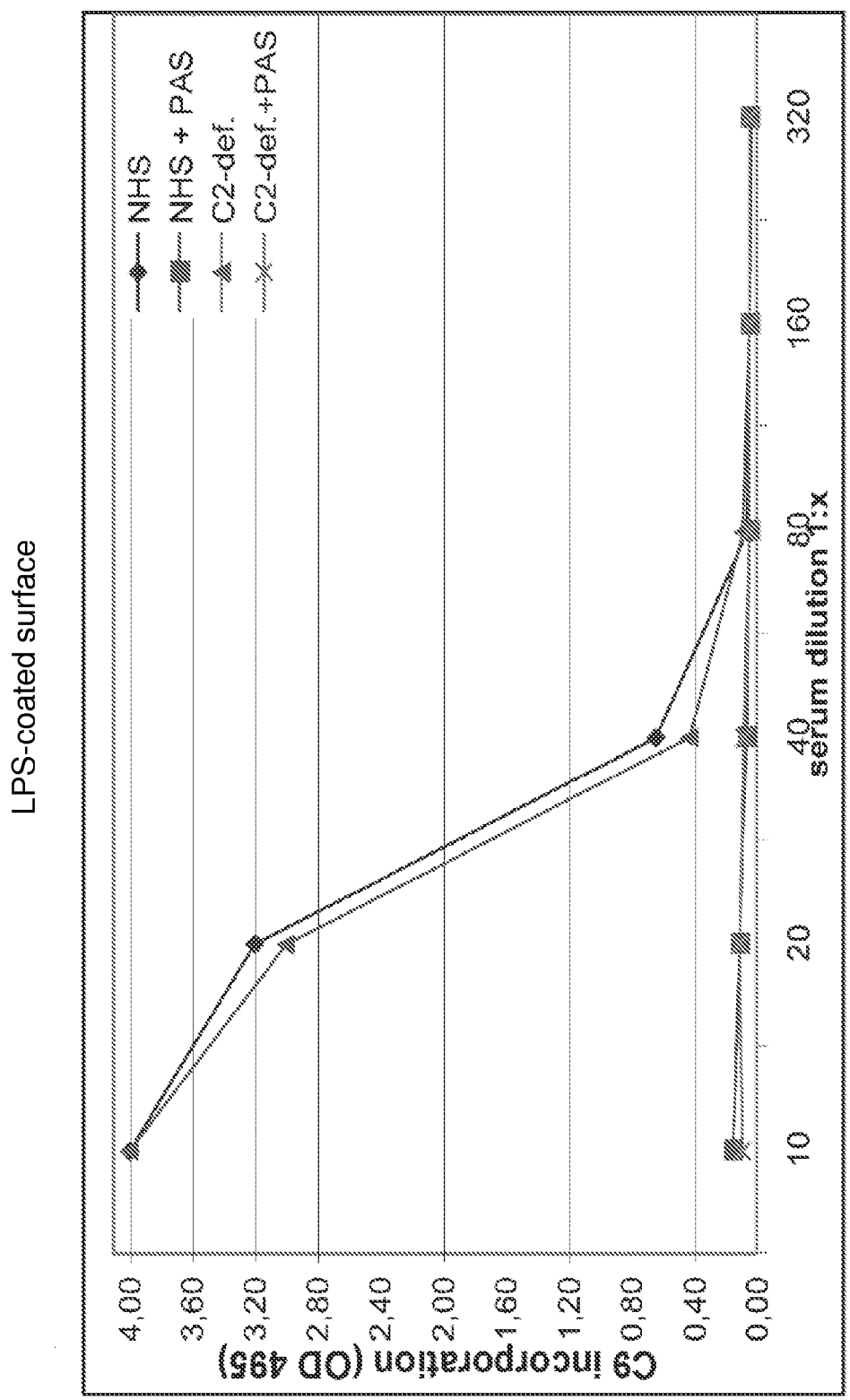

The influence of PAS on complement activation via the AP was also analyzed. NHS and C2-deficient serum diluted in dilution buffer containing 4 mM $Mg^{2+}$ and 10 mM EGTA was incubated in microtiter-wells (PolySorp), coated with LPS as described above in the presence or absence of PAS and deposition of complement components (C3b/C3bi, properdin and C9) was detected. Incubation of NHS and C2-deficient serum in the absence of PAS resulted in a dose-dependent deposition of C3, properdin and C9 (FIG. 5 a-c). In contrast, the serum samples in the presence of PAS resulted in complete inhibition of the deposition of C3, properdin and C9. Thus, like for the CP, the activation of complement through the AP is also inhibited in the presence of PAS.

FIG. 5 shows the activation of the alternative pathway on a LPS-coated surface. Dilutions of NHS and C2-deficient serum in $Mg^{++}$-EGTA-buffer were incubated on plates coated with LPS in the presence or absence of PAS. Deposition of C3 (A), Properdin (B) and C9 (C) was subsequently assessed. Deposition of all three complement components was reduced to background levels when 10 mM EDTA was present in the dilution buffer (not shown).

Figure 6:
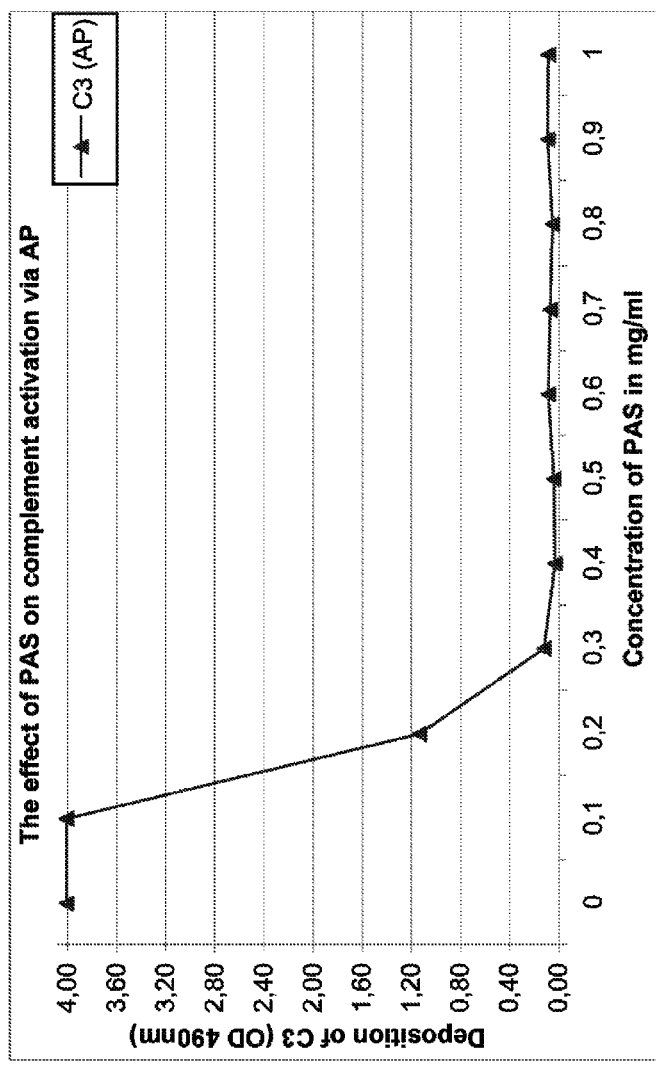
FIG. 6 shows a dose-response curve for the effect of PAS on activation of alternative complement functional activity.
Figure 7A:
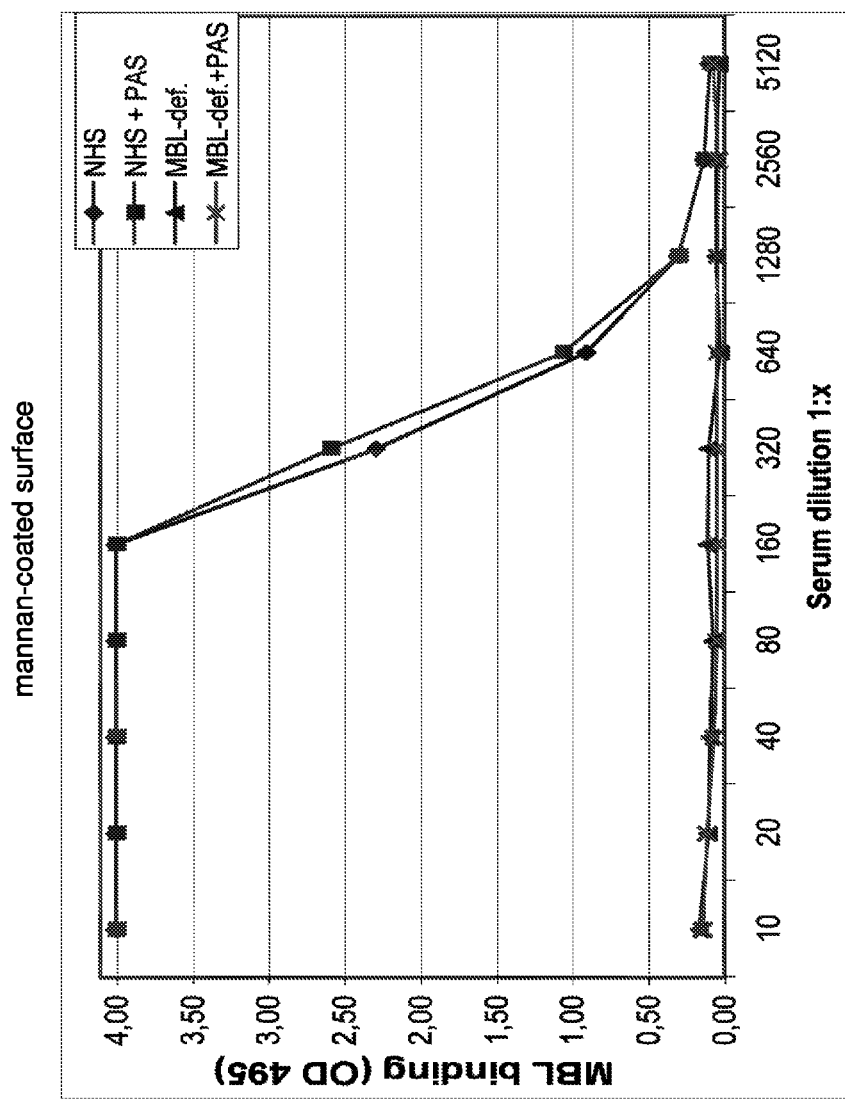
FIG. 7 shows lectin pathway complement activation by mannan coated surfaces. The effect of adding PAS (500 μg/ml) to serum was analyzed by incubating serum dilutions on mannan coated surfaces. Binding of MBL and deposition of complement factors C3, C4, and C9 was demonstrated with specific MAb's.
Figure 7B:
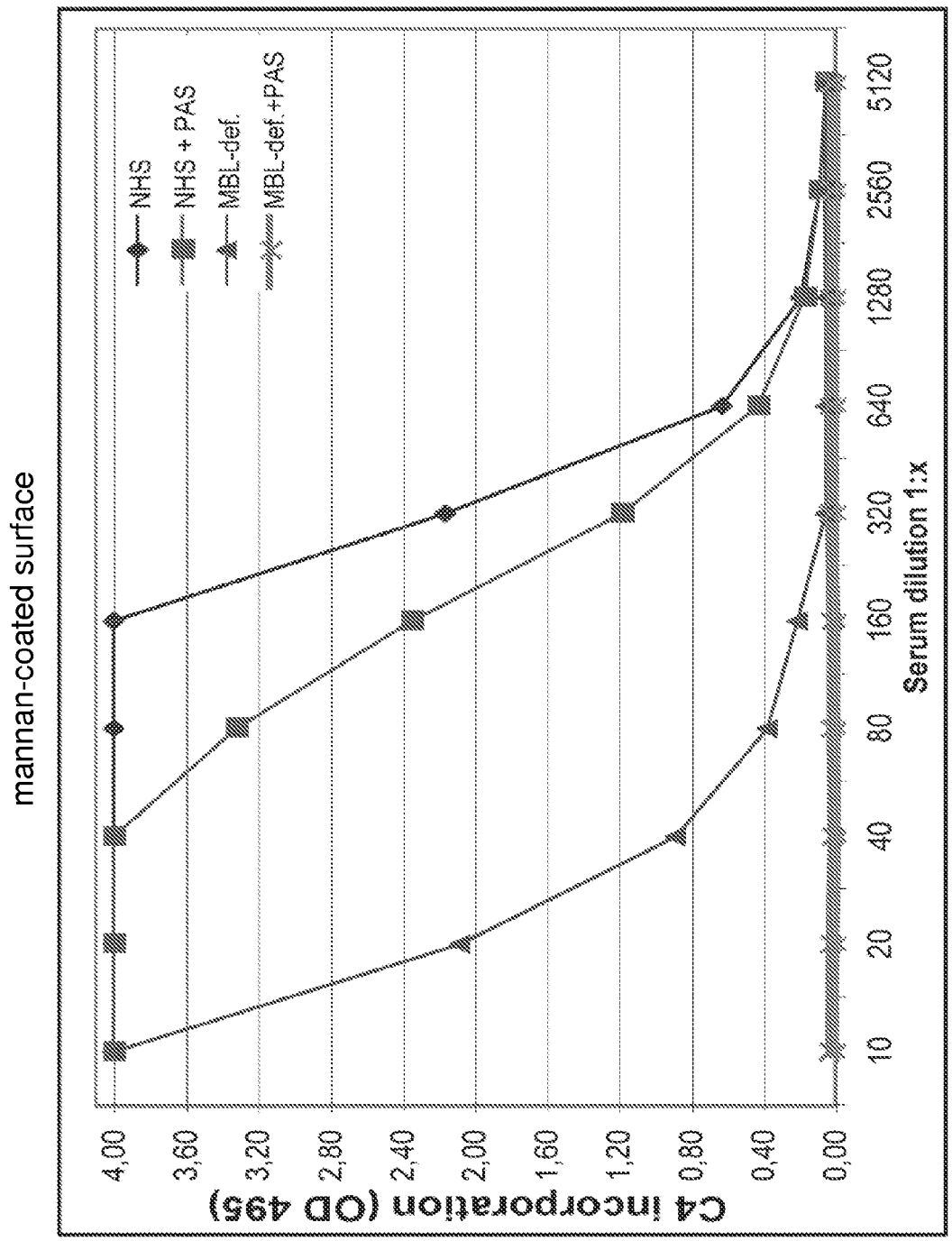
Figure 7C:
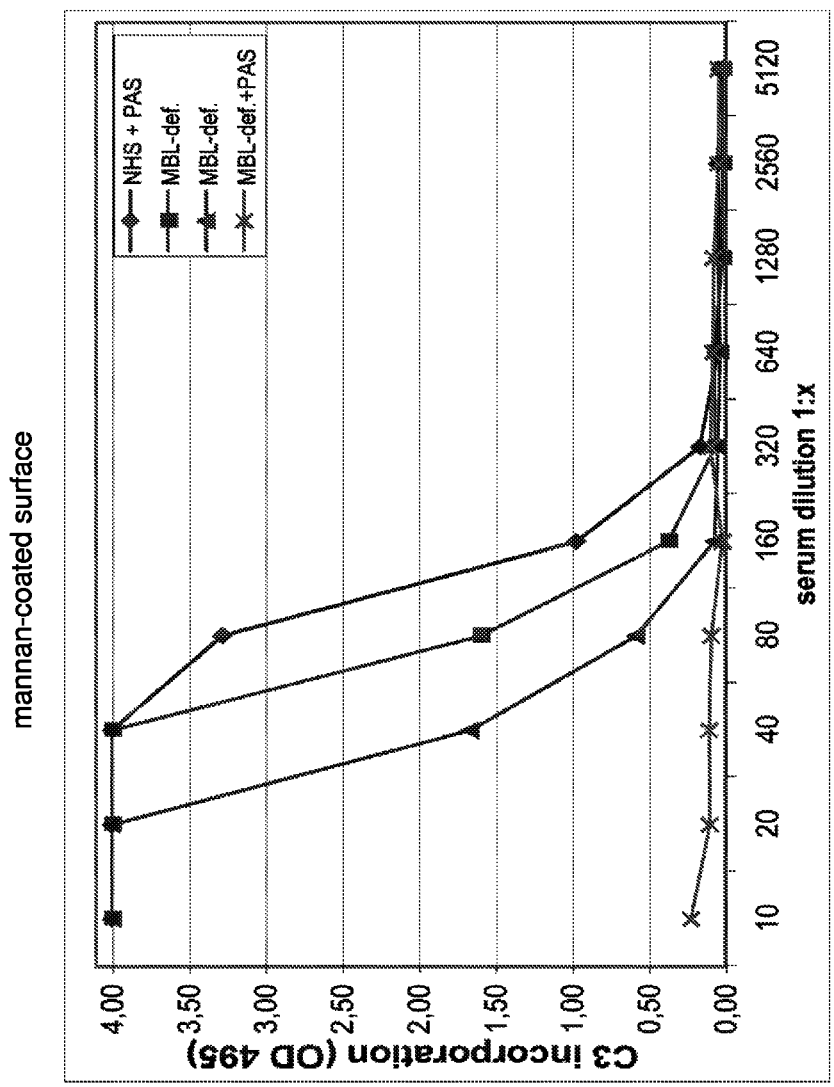
Figure 7D:
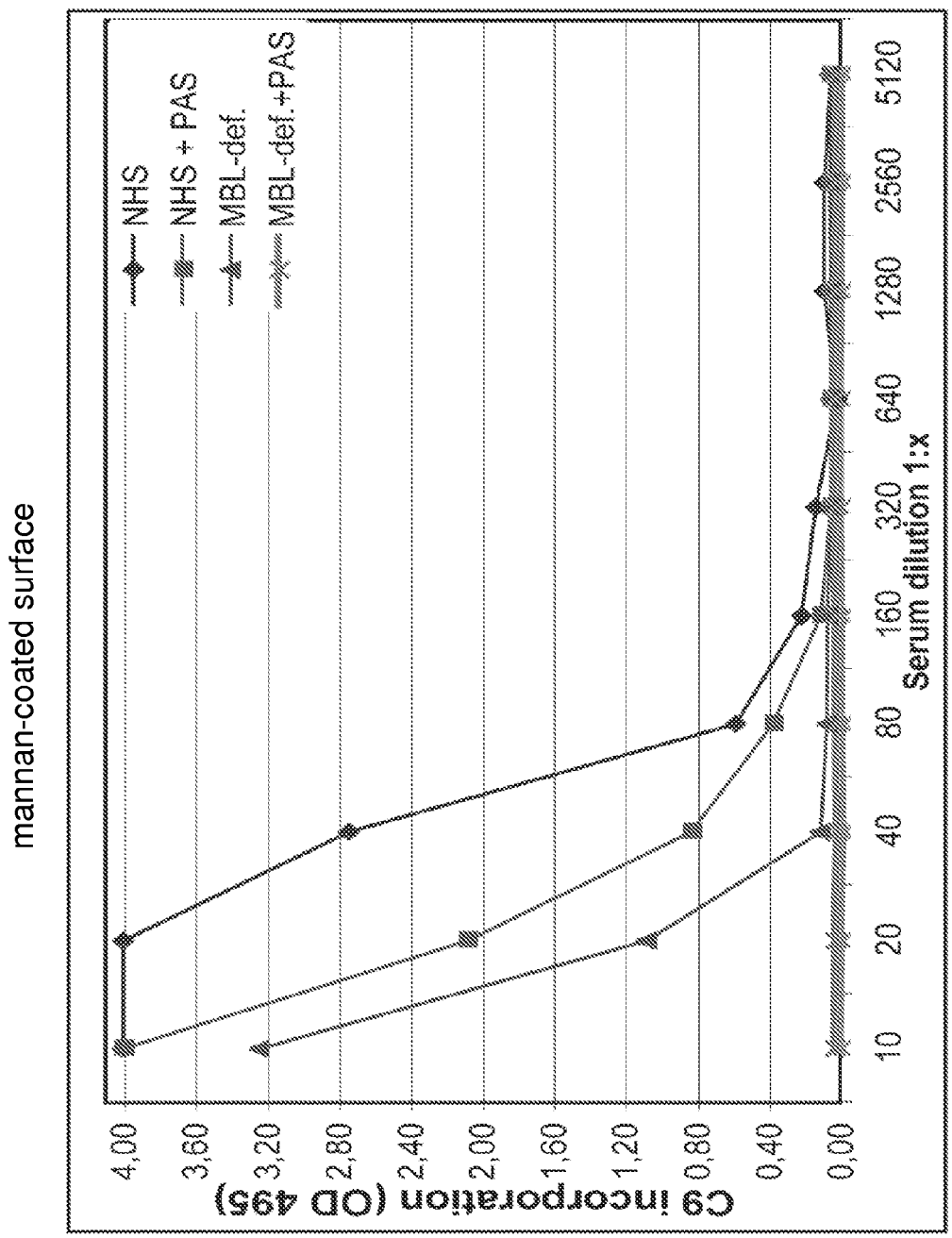

Dose-Response Curve for the Inhibition of Alternative Complement Functional Activity by PAS Various concentrations of PAS were used in order to determine a dose-response curve for PAS. Experiments were performed as described above only with varying the amount of PAS added to the sample. PAS-concentrations >300 µg/ml completely inhibited C3 deposition. Only an example where deposition of C3 is measured is shown, but identical results were obtained when properdin or C9 deposition were analysed. FIG. 6 shows the dose-response curve.

Example 3

Assessment of the Functional MBL Pathway Capacity

To measure the MBL pathway, mannan (SIGMA®, 7250) was used as a ligand. Mannan was dissolved in PBS (10 mg/ml) and stored at 4° C. The microtiter plates (Nunc, Roskilde, Denmark) were coated with 100 µl mannan (100 µg/ml) in coating buffer o/n at 4° C. or for 2 hours at 37° C. The plates were emptied, washed and the residual binding sites were blocked by incubation dilution buffer for 30 min at RT. Serum samples were diluted in dilution buffer containing 4 mMCa2+, 2 mM Mg2+, 0.05% Tween in the presence of PAS (500 µg/ml), pre-incubated for 10 min on ice, and then added at different concentrations to the mannan coated plates. The plates with serum were then incubated 2 h at 37° C. and for 90 min. After wash, detection of MBL, C4, and C3 was performed by addition of 100 µl of mAbs against human MBL (pool of Hyb 131-10 and 131-11), mAb against human β-chain of C4 (Hyb 162-02), mAb against human β-chain of C3b (HAV 3-4) and mAb against C9 (Hyb 04-22) respectively. Binding of mAb was detected using HRP-conjugated polyclonal mouse anti-immunoglobulin (P260, DAKO, Glostrup). After wash the plates were developed, stopped and OD values were determined Effect of PAS on the Lectin Complement Pathway The above examples have shown that PAS inhibits both the CP and the AP. The effect of PAS on the lectin pathway was analysed in analogous experiments where dilutions of NHS or MBL-deficient serum were incubated in the presence or absence of PAS on Maxisorp ELISA plates coated with mannan. The deposition of the complement system components MBL, C4, C3 and C9 were detected by using specific MAb's. The results from these experiments are shown in FIG. 7.

Incubation of NHS on a mannan-coated surface resulted in a dose-dependent binding of MBL, C4, C3 and C9. Binding of MBL in the presence of PAS shows no difference, whereas depositions of C4, C3 and C9 are slightly reduced. This reduction is due to the effect of PAS on simultaneous activation of the CP and AP (as clearly shown when MBL-deficient serum is assayed with or without PAS). These experiments suggest that addition of PAS in serum allows for a detection of the LP activation using mannan as an activating surface, in contrast to detection of CP and AP on appropriate activating surfaces where the presence of PAS results in complete inhibition. MBL deficient serum (from a donor with B/B genotype) shows no binding of MBL to mannan but deposition of C3, C4, and C9. This deposition is abolished with serum incubated with PAS.

FIG. 7: The effect on the activity of the LP of adding PAS (500 µg/ml) to serum was analyzed by incubating serum dilutions on mannan coated surfaces. Binding of MBL and deposition of complement factors C3, C4, and C9 was demonstrated with specific MAb's.

Figure 8:
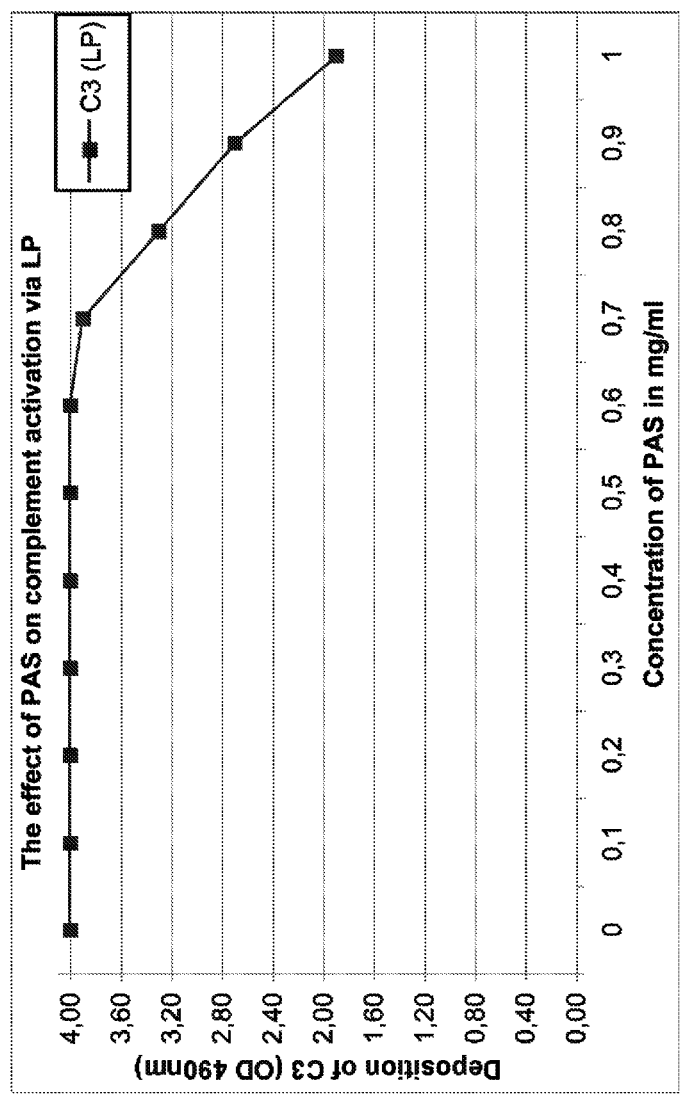
FIG. 8 shows a dose-response curve for the effect of PAS on activation of lectin complement functional activity.

Dose-Response Curve for the Inhibition of Lectin Complement Pathway Functional Activity by PAS Various concentrations of PAS were used in order to determine a dose-response curve for PAS. Experiments were performed as described above only with varying the amount of PAS added to the sample. Only PAS-concentrations >700 µg/ml slightly inhibited C3 deposition. Only an example where deposition of C3 is measured is shown, but identical results were obtained when C4 or C9 deposition were analysed. FIG. 8 shows the dose-response curve.

Example 4

Figure 9:
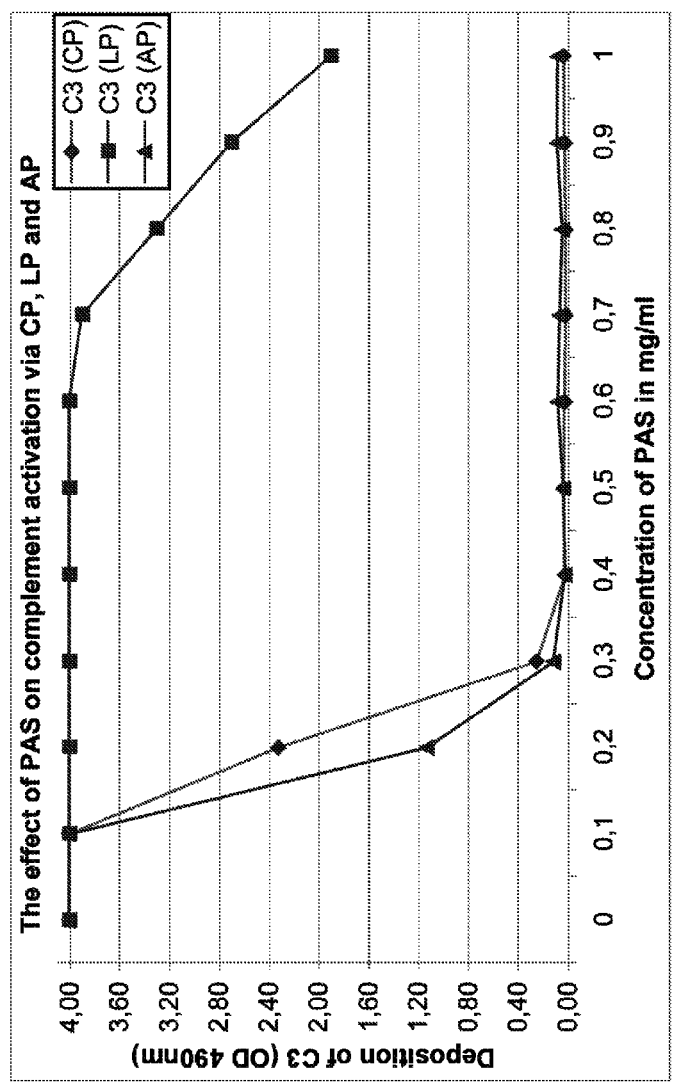
FIG. 9 shows a combined dose-response curve for the effect of PAS on activation of functional activity of the three individual complement pathways.

Comparison of Dose-Response Effect of PAS on Functional Complement Activity of the Three Individual Complement Pathways In order to more clearly illustrate and define a concentration of PAS where both classical and alternative pathway activation is totally inhibited but lectin complement pathway is unaffected, the three dose-response curves from the three examples shown above are combined in a single figure (FIG. 9). The figure shows that PAS can be used within the dose-interval 300-700 µg/ml to analyse for lectin pathway functional activity. The preferred concentration has been chosen to be 500 µg/ml.

Example 5

Figure 10:
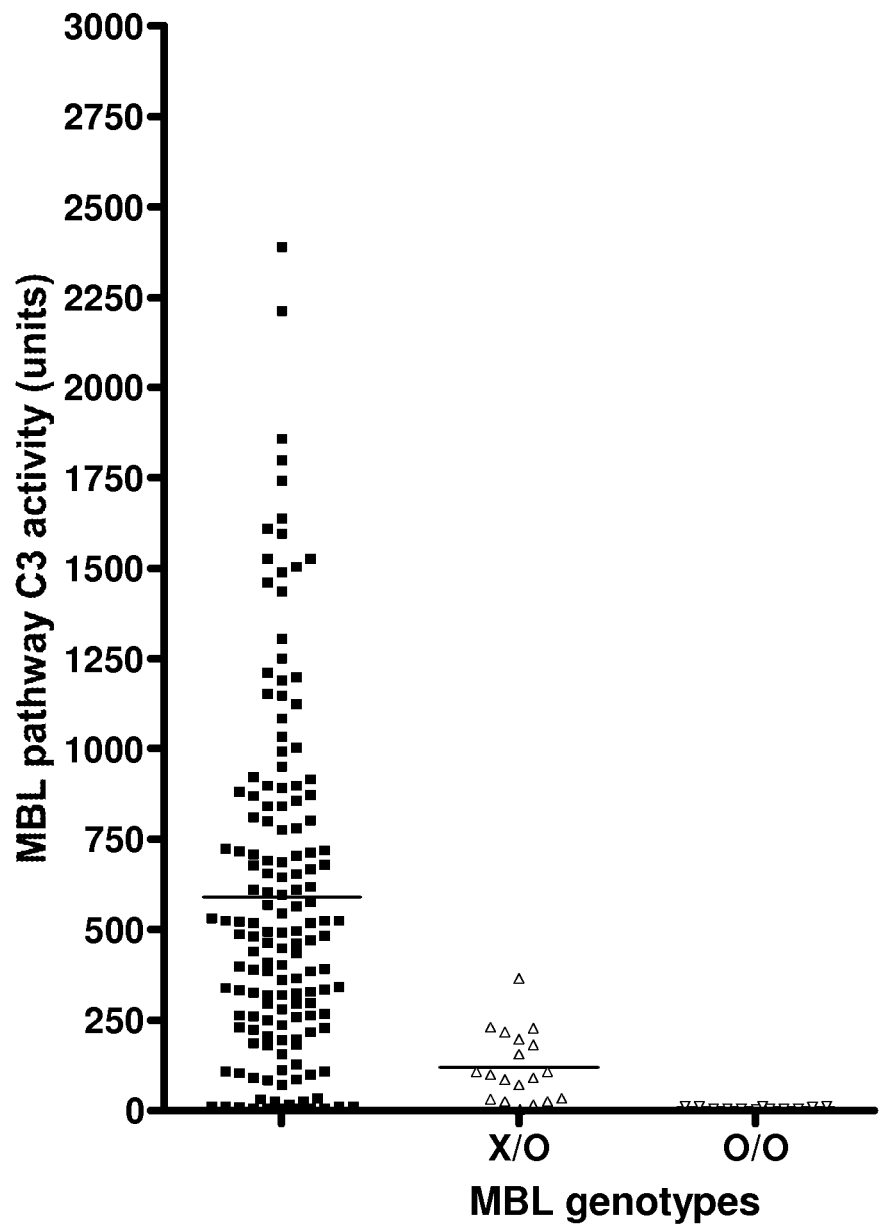
FIG. 10 shows in the first column the MBL pathway C3 activity from a population of 150 healthy blood donors, the activity is given in arbitrary units. The second column (X/O) and third column (O/O) is individuals heterozygous or homozygous for MBL structural mutations, respectively.

Distribution of LP Functional Activity Among 150 Normal Individuals (Healthy Blood Donors) and in Two Selected Groups with Functional Deficiencies in the LP 150 healthy blood donors were assayed in the described assay for LP activity. Serum dilutions were 1:10 and PAS was added to a final concentration 500 µg/ml. FIG. 10 first column shows the LP functional activity as monitored as incorporation of C3. Activity is given as arbitrary units. Functional activity in individuals heterozygous for MBL structural mutations (carrying the wild-type gene (A) on one chromosome, and a structural mutation (B, C, or D) on the other chromosome) is indicated as X/O on the figure. Functional activity in individuals homozygous for one single or combinations of the structural mutations B, C, and D is indicated as O/O on the figure.

Figure 11:
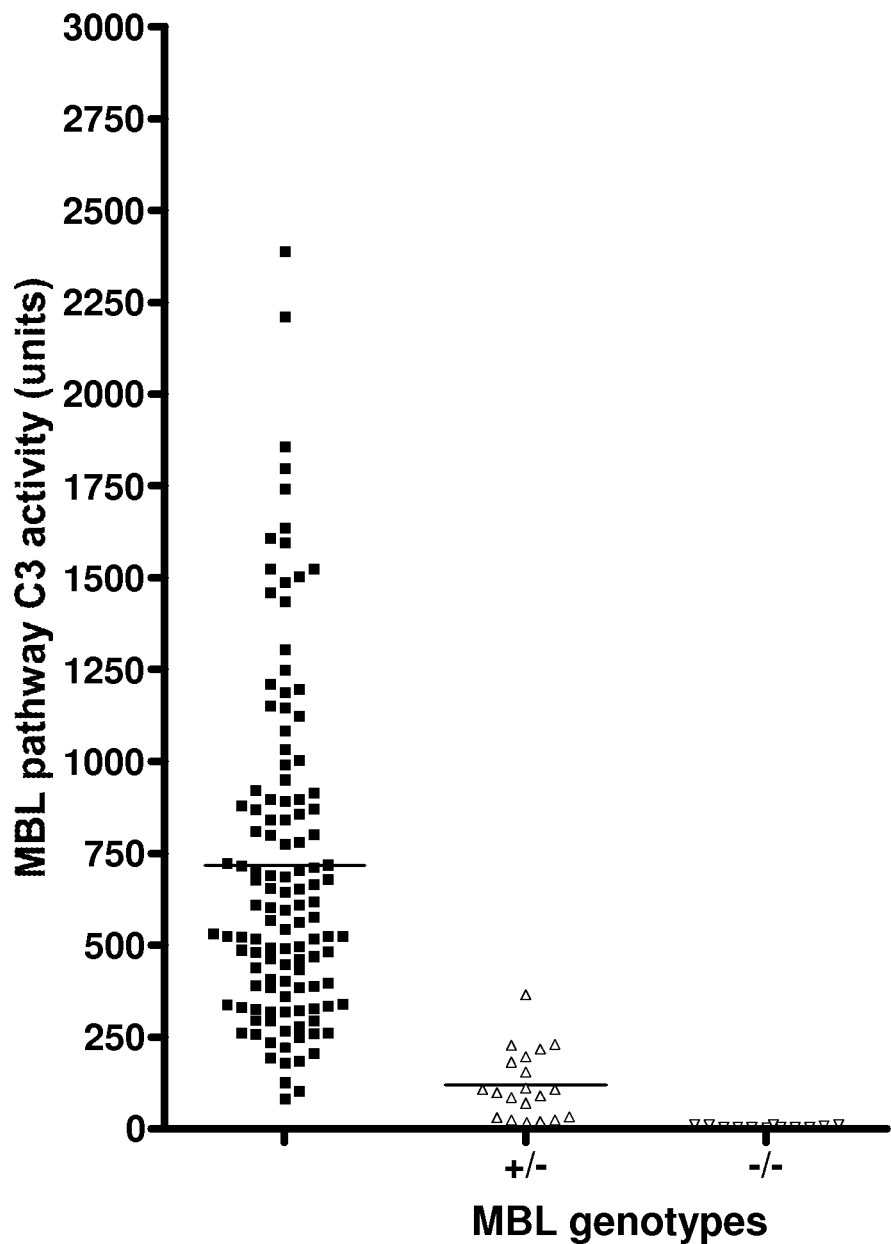
FIG. 11 shows in the first column the MBL pathway C3 activity from a population of 150 healthy blood donors, where individuals heterozygous or homozygous for MBL structural mutations have been removed. The activity is given in arbitrary units. The second column (+/−) and third column (−/−) is individuals heterozygous or homozygous for MBL structural mutations, respectively.

FIG. 11 gives the data as in FIG. 10, however with the difference that the first column show the LP functional activity of the donors, where individuals heterozygous or homozygous for MBL structural mutations have been removed from the data set, hereby giving a different average value for LP functional activity. The first column does however contain data for individuals with promoter region mutations. Accordingly, FIG. 10 and FIG. 11 show in their first columns two different ways to provide population to be used as reference populations for definition of a reference value for measurements according to the method of the present invention.

Figure 12:
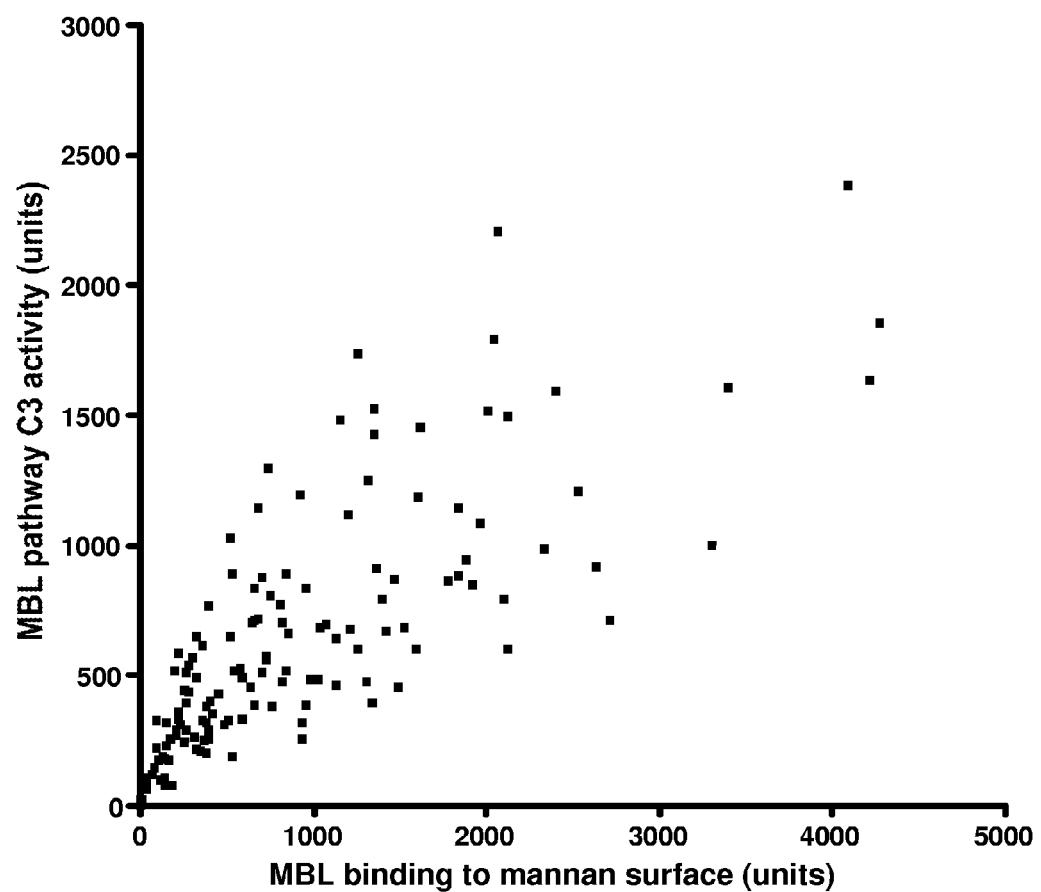
FIG. 12 shows a correlation between MBL pathway C3 activity and MBL binding to a mannan surface, among 150 healthy blood donors.

The arbitrary units applied in FIGS. 10, 11, and 12 arise from ELISA optical densities which are correlated to an in-house working standard (homozygous wild type A/A donor without promotor mutations), which was given a value of 1000 units.

Example 6

Correlation Between LP Functional Activity and Binding of MBL to a Mannan Surface 150 healthy blood donors were assayed in the described assay for LP activity. Serum dilutions were 1:10 and PAS was added to a final concentration 500 µg/ml. Activity was monitored as incorporation of C3. Activity is given as arbitrary units. The same donors were assayed in an assay for binding of MBL to a mannan surface. A polystyrene ELISA-plate was coated with mannan, 10 µg/ml, and incubated with a dilution 1:50 of the individual donors (diluted in a TBS-Ca++-buffer). Binding of MBL was measured with an anti MBL monoclonal antibody (HYB 131-10). MBL concentrations were determined by comparison with a purified MBL preparation as a standard.

FIG. 12 shows the correlation in individual donors, and statistical analysis showed a significant correlation between functional capacity and MBL concentrations (R=0.6389, P<0.001). However, in some sera samples low functional capacity correlated with normal MBL concentration, indicating individuals with functional deficiencies in other components of the LP (e.g. MBL associated serine proteases). The method according to the present invention will, due to the measurement of one or more of the complement factors C3, C4, or one or more of the components of the C5-C9 complex, be able to determine functional deficiencies in the lectin pathway of such individual with a normal MBL concentration.

The invention claimed is:

1. A method of in vitro determining functional deficiencies in the lectin pathway of the complement system, the method comprises the steps of
    (a) diluting a mammalian sample of body fluid with a diluent comprising polyanethol sulphonate (PAS) in a concentration range of from about 50 to about 1000 µg/ml;
    (b) activating the lectin pathway of the complement system in the sample obtained from (a); and
    (c) determining in the sample obtained from (b), the activation of one or more of the complement factors C3, C4, or one or more of the components of the C5-C9 complex comprising contacting the sample obtained from (b) with an antibody to one or more of the activated complement factors C3 or C4, or one or more of the components of the C5-C9 complex; and
    (d) comparing the determined activation level of one or more of the complement factors C3, C4, or one or more of the components of the C5-C9 complex with a reference level, wherein a lower activation level in the sample relative to the reference level is indicative of a functional deficiency in the lectin pathway.

2. The method according to claim 1, wherein the mammalian sample of body fluid is a human sample of body fluid.

3. The method according to claim 1, wherein the sample of body fluid is a sample of blood, plasma or serum.

4. The method according to claim 3, wherein the sample of body fluid is a sample of blood.

5. The method according to claim 1, wherein the concentration of polyanethol sulphonate (PAS) in the diluent is in a range of from about 300 to about 700 µg/ml.

6. The method according to claim 1, wherein the concentration of polyanethol sulphonate (PAS) in the diluent is in a range of from about 400 to about 600 µg/ml.

7. The method according to claim 1, wherein the concentration of polyanethol sulphonate (PAS) in the diluent is about 500 µg/ml.

8. The method according to claim 1, wherein the diluent is an aqueous media.

9. The method according to claim 1, wherein the diluent is buffered to physiological pH with a buffer.

10. The method according to claim 1, wherein the diluent contains $Ca^{2+}$ and $Mg^{2+}$.

11. The method according to claim 10, wherein the diluent comprises a concentration of $Ca2+$ from about 2 to about 6 mM and a concentration of $Mg2+$ from about 0.5 to about 4 mM.

12. The method according to claim 10, wherein the diluent comprises a concentration of $Ca2+$ from about 3 to about 5 mM and a concentration of $Mg2+$ from about 1 to about 3 mM.

13. The method according to claim 10, wherein the diluent comprises a concentration of $Ca2+$ of about 4 mM and a concentration of $Mg2+$ of about 2 mM.

14. The method according to claim 1, wherein the diluent comprises Tween in a concentration range of from about 0.02% to about 0.40%.

15. The method according to claim 1, wherein the diluent comprises Tween in a concentration range of from about 0.02% to about 0.30%.

16. The method according to claim 1, wherein the diluent comprises Tween in a concentration range of from about 0.02% to about 0.20%.

17. The method according to claim 1, wherein the diluent comprises Tween in a concentration range of from about 0.01% to about 0.50%.

18. The method according to claim 1, wherein the diluent comprises Tween 20 in a concentration of about 0.05%.

19. The method according to claim 1, wherein the diluent is an isotonic aqueous media with a pH-value of about physiological pH.

20. The method according to claim 1, wherein the diluent is a buffered aqueous media comprising $Ca^{2+}$ and $Mg^{2+}$ in concentrations of about 4 mM, and about 2 mM, respectively, and comprising Tween 20 in a concentration of about 0.05%.

21. The method according to claim 1, wherein the dilution in step (a) is performed with an incubation time of less than 30 min.

22. The method according to claim 1, wherein the activation in step (b) is performed with an incubation time of from about 10 minutes to about 3 hours.

23. The method according to claim 1, wherein the activation in step (b) is performed with an incubation time of from about 30 minutes to about 2.5 hours.

24. The method according to claim 1, wherein the activation in step (b) is performed with at an incubation temperature of about 37° C.

25. The method according to claim 1, wherein step (b) is performed by contacting the sample obtained from (a) with a lectin binding surface comprising carbohydrate structures.

26. The method according to claim 1, wherein step (b) is performed by contacting the sample obtained from (a) with a MBL binding surface.

27. The method according to claim 26, wherein the MBL binding surface is a mannan.

28. The method according to claim 1, wherein step (b) is performed by contacting the sample obtained from (a) with a ficolin binding carbohydrate.

29. The method according to claim 1, wherein the activation of complement factor C3 is determined in step (c).

30. The method according to claim 1, wherein the antibody is a labelled antibody.

31. The method according to claim 30, wherein the labelled antibody is labelled with a fluorescent label or an enzyme label.

32. The method according to claim 1, wherein the anti-C3, -C4, or -C5-C9 complexes obtained in step (c) may be detected by the use of labelled anti-antibodies against one or more of the anti-C3, or -C4, or against antibodies against one or more of the components of the C5-C9 complex.

33. The method according to claim 1, wherein the reference level is an average value obtained from healthy individuals.

34. The method according to claim 33, wherein an activation level at least 35% lower than a reference level obtained from the general healthy population is indicative of a functional deficiency in the lectin pathway.

35. The method according to claim 1, wherein the diluent comprises Tween in a concentration range of from about 0.03% to about 0.10%.

36. The method according to claim 1, wherein the diluent comprises Tween in a concentration of about 0.05%.

37. The method according to claim 1, wherein the dilution in step (a) is performed with an incubation time of less than 20 min.

38. The method according to claim 1, wherein the dilution in step (a) is performed with an incubation time of less than 10 min.

39. The method according to claim 1, wherein the activation in step (b) is performed with an incubation time of from about 45 minutes to about 2 hours.

40. The method according to claim 1, wherein the activation in step (b) is performed with an incubation time of about 90 minutes.

* * * * *